United States Patent
Benz et al.

(10) Patent No.: US 8,835,526 B2
(45) Date of Patent: *Sep. 16, 2014

(54) POLYMERS FOR INTRAOCULAR LENSES

(71) Applicant: Benz Research and Development Corporation, Sarasota, FL (US)

(72) Inventors: Patrick H. Benz, Sarasota, FL (US); Jose A. Ors, Sarasota, FL (US)

(73) Assignee: Benz Research and Development Corporation, Sarasota, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/680,755

(22) Filed: Nov. 19, 2012

(65) Prior Publication Data
US 2013/0178555 A1    Jul. 11, 2013

Related U.S. Application Data

(60) Continuation of application No. 12/126,701, filed on May 23, 2008, now Pat. No. 8,318,832, which is a division of application No. 11/402,642, filed on Apr. 12, 2006, now Pat. No. 7,387,642.

(60) Provisional application No. 60/671,002, filed on Apr. 13, 2005.

(51) Int. Cl.
| | |
|---|---|
| *G02B 1/04* | (2006.01) |
| *C08F 18/02* | (2006.01) |
| *C08F 220/26* | (2006.01) |
| *C08F 220/28* | (2006.01) |
| *C08F 216/02* | (2006.01) |
| *C08L 29/10* | (2006.01) |
| *A61F 2/16* | (2006.01) |
| *B29D 11/02* | (2006.01) |
| *A61L 27/16* | (2006.01) |
| *C08F 22/14* | (2006.01) |
| *C08F 222/10* | (2006.01) |

(52) U.S. Cl.
CPC ........... *C08F 22/14* (2013.01); *C08F 222/1006* (2013.01); *A61F 2/16* (2013.01); *B29D 11/023* (2013.01); *A61L 27/16* (2013.01); *C08F 220/28* (2013.01)
USPC ........... 523/113; 523/106; 256/319; 256/320; 256/329.6; 256/332; 525/79; 525/312

(58) Field of Classification Search
USPC ............. 523/113, 106; 525/79, 312; 526/319, 526/320, 329.6, 332
See application file for complete search history.

(56) References Cited

U.S. PATENT DOCUMENTS 3,780,003 A * 12/1973 Seymour et al. .............. 526/320
4,038,264 A   7/1977 Rostoker et al.

(Continued)

FOREIGN PATENT DOCUMENTS

| EP | 0 485 197 | 5/1992 |
| GB | 2196973 | 5/1988 |
| WO | WO 90 09230 | 8/1990 |

OTHER PUBLICATIONS

"Cytotoxic effects of residual chemicals from polymeric biomaterials for artificial soft intraocular lenses," J. Cataract Refract. Surg., vol. 17, Mar. 1991.

(Continued)

Primary Examiner — Michael Pepitone
(74) Attorney, Agent, or Firm — Foley & Lardner LLP

(57) ABSTRACT

The present invention provides optic portions, intraocular lenses, and polymers for use in manufacturing optic portions and intraocular lenses. The optic portions include a polymer that comprises (a) one or more alkoxyalkyl methacrylate monomers and/or one or more alkoxyalkyl acrylate monomers that are incorporated in the polymer; (b) one or more hydroxyalkyl methacrylate monomers and/or one or more hydroxyalkyl acrylate monomers that are incorporated in the polymer; and (c) optionally, one or more crosslinking agents that are incorporated in the polymer.

15 Claims, 3 Drawing Sheets

(56) References Cited

U.S. PATENT DOCUMENTS

| | | | |
|---|---|---|---|
| 4,379,864 | A | 4/1983 | Gallop et al. |
| 4,388,448 | A | 6/1983 | Melby |
| 4,582,884 | A | 4/1986 | Ratkowski |
| 4,718,906 | A | 1/1988 | Mackool |
| 4,764,169 | A | 8/1988 | Grendohl |
| 4,769,431 | A | 9/1988 | Ratkowski |
| 4,866,148 | A | 9/1989 | Geyer et al. |
| 5,080,482 | A | 1/1992 | Benz et al. |
| 5,147,902 | A | 9/1992 | Ichikawa et al. |
| 5,217,491 | A | 6/1993 | Vanderbilt |
| 5,326,506 | A | 7/1994 | Vanderbilt |
| 5,330,911 | A | 7/1994 | Hubbell et al. |
| 5,480,950 | A | 1/1996 | Wang et al. |
| 5,507,805 | A | 4/1996 | Koeniger |
| 5,532,289 | A | 7/1996 | Benz et al. |
| 5,674,557 | A * | 10/1997 | Widman et al. ............. 427/133 |
| 5,891,932 | A | 4/1999 | Benz et al. |
| 6,011,081 | A | 1/2000 | Benz et al. |
| 6,242,508 | B1 | 6/2001 | Benz et al. |
| 6,245,830 | B1 | 6/2001 | Benz et al. |
| 6,265,465 | B1 | 7/2001 | Benz et al. |
| 6,267,784 | B1 | 7/2001 | Benz et al. |
| 6,517,750 | B2 | 2/2003 | Benz et al. |
| 7,067,602 | B2 | 6/2006 | Benz et al. |
| 2002/0032620 | A1 | 3/2002 | Benz et al. |
| 2002/0037984 | A1 | 3/2002 | Vanderbilt |
| 2005/0131183 | A1 | 6/2005 | Benz et al. |
| 2006/0199929 | A1 | 9/2006 | Benz et al. |

OTHER PUBLICATIONS

Benz et al., "New Materials Demand More Accurate Measurements of Performance," Contact Lens Spectrum, Jul. 1997, pp. 40-46.
International Search Report dated Sep. 15, 2006 for PCT/US2006/013730.
Kloosterboer et al., "Photopolymerizable Lacquers for LaserVision Video Discs," Phillips Tech. Rev. 40, 298-309 (1982).
Macret et al., "Hydroxyalkyl methacrylates: hydrogel formation based on the radical copolymerization of 2-hydroxyalkyl-methacrylate and 2,3-dihydroxypropyl-methacrylate" *Polymers* 23:748-753 (1982).
Macret et al., "Hydroxyalkyl methacrylates: Kinetic investigations of radical polymerizations of pure 2-hydroxyethyl methacrylate and 2,3-dihydroxypropyl methacrylate and the radical copolymerization of their mixtures" *Polymer* 23:81-90 (1982).
N. Pescosolido, et al., "Nuclear Magnetic Resonance Study of Dehydration in a Glyceryl-Methyl-Methacrylate Contact Lens," Contactologia, 1993, pp. 64-67.
Ors et al., "Effects of Monomer Interaction on Polymer Cure," Proceedings of ACS Division of PMSE 56, 744 (1987).
Refojo, "Hydrogels from 2-Hydroxyethyl Methacrylate and Propylene Glycol Monoacrylate" *Journal of App. Pol. Sci.* 9:2425-2434 (1965).
Urs Businger, "GMA/HEMA: First Report on a Clinical Trial," Contact Lens Spectrum, Aug. 1995, pp. 19-26.
Yasuda et al., "Hydrogels of Poly(hydroxyethyl Methacrylate) and Hydroxyethyl Methacrylate-Glycerol Monomethacrylate Copolymers" *Journal of Pol. Sci. Part A-1* 4:2913-2927 (1996).

\* cited by examiner

POLYMERS FOR INTRAOCULAR LENSES

CROSS-REFERENCE TO RELATED PATENT APPLICATIONS

This application is a continuation of U.S. application Ser. No. 12/126,701, filed May 23, 2008, and subsequently issued as U.S. Pat. No. 8,318,832, which is a divisional of U.S. application Ser. No. 11/402,642, filed Apr. 12, 2006, and subsequently issued as U.S. Pat. No. 7,387,642, which claims priority benefit under 35 U.S.C. 119(e) to U.S. Application Provisional Application No. 60/671,002, filed Apr. 13, 2005, each incorporated herein by reference in their entirety.

FIELD OF THE INVENTION

This invention relates to polymers for use in making optic portions of intraocular lenses and intraocular lenses. More specifically, the invention relates to polymers formed from one or more alkoxyalkyl acrylate and/or an alkoxyalkyl methacrylate monomers and a hydrophilic monomer or monomers such as 2-hydroxyethyl methacrylate (HEMA). The invention also relates to intraocular lenses made from the polymers, and methods of making such lenses.

BACKGROUND OF THE INVENTION

Various types of intraocular lenses (IOLs) are known. For example, both one-piece intraocular lenses and composite intraocular lens having multiple pieces are known. A one-piece intraocular lens is one where both optic and non-optic portions are made from one material. The non-optic portions of IOLs are referred to as haptic portions, and are used for attachment purposes. Two general designs for the haptics are a "plate-type" and a "C-haptic" type, both of which may have a variety of shapes. A plate design is shown in FIGS. 1A and 1B. A "C" design is shown in FIGS. 2A and 2B. These Figures are discussed in greater detail below.

IOLs with mechanically-attached haptics are lenses where the optic-portion and the haptic-portion are made separately, usually from different materials, and attached. For example, the lens portion can be made of a hydrogel or silicone-based material and the C-shape haptics from a rigid material like poly(methyl methacrylate) (p-MMA), polyvinylidene fluoride (PVDF), and polysulfones. The p-MMA haptics may be attached to the optic portion using holes drilled into the optic portion.

Although traditional hydrophobic intraocular lenses are made from p-MMA, they are not easily foldable and require a relatively large incision for insertion. To make hydrophobic materials foldable, rubber-like materials, such as silicone derivatives, have been included in the rigid polymer matrix or materials consisting primarily of silicone derivatives have been used. Although the softness of a primarily silicone material is ideal for folding prior to insertion, when the lens and its haptics unfold in the eye, the almost gel-like softness of the lens makes it difficult for a surgeon to properly position the lens in the eye. Furthermore, the silicone lens often does not provide sufficient rigidity for the lens after insertion and the combination of deformation from compressive forces along with lens movement can produce lens distortion and compromise the optical integrity of the lens.

Because of its inherent properties, p-hydroxyethyl methacrylate (a homopolymer of HEMA) has been used as a foldable material for intraocular lenses. However, the low refractive index of p-HEMA, when hydrated, leads to limitations in the optical center design and a compromise between its folding ability and its optical requirements.

One of the limitations of one-piece p-HEMA hydrogel lenses has been that the haptic portion lacks the desired modulus and can, therefore, compromise lens positioning. To address this issue, polymer materials have been combined to give a soft, foldable intraocular composite lens such as p-HEMA or other soft acrylic material for the optic zone, and a rigid structure around the outside of the lens, made from a hard plastic such as p-MMA. See U.S. Pat. No. 4,718,906 and U.S. Pat. No. 5,326,506, both hereby incorporated by reference in their entireties, which describe composite intraocular lenses. These multicomponent materials are made by embedding one material in the other, by concurrent extrusion processes, by solidifying the hard material about the soft material, or by forming an interpenetrating network of the rigid component into a preformed hydrophilic core.

IOLs made from hydrophilic materials (hydrogels) have shown appropriate biocompatibility in the eye capsule. The most common hydrophilic IOL materials range in water content between 24 and 28%. This water level imparts the right range of mechanical properties that allow lenses to be easily folded, placed in small diameter injectors, and introduced into the capsular bag through incision sizes at or below 1.5 mm.

On the other hand, hydrophobic materials (generally less than about 4% water), may have desirable mechanical properties for use in manufacturing IOLs. Aside from mechanical properties, IOLs made from hydrophobic materials may exhibit reduced lens opacification rates from either posterior chamber opacification (PCO) following cataract surgery or due to calcium deposits in the lens matrix. For this reason, the development of new hydrophobic polymers with suitable properties such as foldability, unfoldability, and refractive index is important as these may be used to manufacture new and improved IOLs.

U.S. Pat. No. 5,326,506, discloses a composite intraocular lens including a soft, pliable inner lens optic using rigid haptics. The lens optic material is a low water content material such as a copolymer of 2-HEMA and hydroxyhexyl methacrylate which has a high refractive index due to its low water content. The hard, yet foldable, P-MMA haptics, are attached by an interpenetrating network.

U.S. Pat. No. 4,764,169, hereby incorporated by reference in its entirety, discloses a composite intraocular lens including a small, hard inner lens optic and a soft, pliable skirt surrounding the lens optic. The lens optic material is a relatively hard material such as P-MMA, polysulfone, or polycarbonate. The soft, pliable skirt is a silicone, hydrogel, or like material.

Although significant strides have been made in the area of materials for use in the manufacture of IOLs, novel polymeric materials with improved properties are still needed for use in manufacturing IOLs with improved mechanical and optical properties.

SUMMARY OF THE INVENTION

The invention provides optic portions, intraocular lenses, polymers, and methods for making polymers, optic portions, and intraocular lenses.

In one aspect the invention provides an optic portion of an intraocular lens. The optic portion includes a polymer that comprises, consists of, or consists essentially of:
(a) one or more alkoxyalkyl methacrylate monomers and/or one or more alkoxyalkyl acrylate monomers that are incorporated in the polymer;

(b) one or more hydroxyalkyl methacrylate monomers and/or one or more hydroxyalkyl acrylate monomers that are incorporated in the polymer; and (c) optionally, one or more crosslinking agents that are incorporated in the polymer. In some embodiments, the total combined weight of the one or more alkoxyalkyl methacrylate monomers and the one or more alkoxyalkyl acrylate monomers ranges from 75 percent to 99 percent based on the total weight of the dry polymer, and the total combined weight of the one or more hydroxyalkyl methacrylate monomers and the one or more hydroxyalkyl acrylate monomers ranges from 1 percent to 25 percent based on the total weight of the dry polymer.

In some embodiments, the invention provides an intraocular lens that includes an optic portion. In some such embodiments, the intraocular lens further includes one or more haptic portion. In some such embodiments, the optic portion and the haptic portion are made of the same polymer. In other embodiments, the optic portion and the haptic portion are made of different materials. In some embodiments, the optic portion and the one or more haptic portions are part of a one piece intraocular lens. In other embodiments, the optic portion and the one or more haptic portions form a multiple piece intraocular lens. In still other embodiments, the intraocular lens further includes a polymer that surrounds the optic portion and is not the same as the polymer of the optic portion.

In other embodiments of the optic portion and the intraocular lens, the one or more alkoxyalkyl methacrylate monomers have the formula $R_1$—O—$R_2$-MA prior to being incorporated in the polymer, and the one or more alkoxyalkyl acrylate monomers have the formula, $R_3$—O—$R_4$-A prior to being incorporated in the polymer, wherein MA is methacrylate, A is acrylate, and $R_1$, $R_2$, $R_3$, and $R_4$ are independently selected from alkyl groups having from 1 to 5 carbon atoms. In some such embodiments, $R_1$ and $R_3$ have from 1 to 3 carbon atoms, and $R_2$ and $R_4$ have 2 or 3 carbon atoms. In other such embodiments, $R_1$ and $R_3$ have 2 carbon atoms, and $R_2$ and $R_4$ have 2 carbon atoms. In some such embodiments, the polymer of the optic portion comprises incorporated ethoxyethyl methacrylate. In some such embodiments, the polymer of the optic portion comprises incorporated ethoxyethyl methacrylate, and the total weight of the ethoxyethyl methacrylate ranges from 80 percent to 98 percent, and in some embodiments, from 86 to 98 percent, based on the total weight of the dry polymer of the optic portion.

In other embodiments of the optic portion and the intraocular lens, the one or more hydroxyalkyl methacrylate monomers have the formula HO—$R_5$-MA prior to being incorporated in the polymer, and the one or more hydroxyalkyl acrylate monomers have the formula, HO—$R_6$-A prior to being incorporated in the polymer, wherein MA is methacrylate, A is acrylate, and $R_5$ and $R_6$ are independently selected from alkyl groups having from 1 to 4 carbon atoms. In some such embodiments, $R_5$ and $R_6$ have from 2 to 3 carbon atoms. In other such embodiments, $R_5$ and $R_6$ have 2 carbon atoms. In some such embodiments, the polymer of the optic portion comprises incorporated 2-hydroxyethyl methacrylate. In some such embodiments, the polymer of the optic portion comprises incorporated 2-hydroxyethyl methacrylate, and the total weight of the 2-hydroxyethyl methacrylate ranges from 1 percent to 20 percent, and in some embodiments, from 1 percent to 12 percent, based on the total weight of the dry polymer of the optic portion.

In some embodiments, the polymer of the optic portion comprises, the one or more crosslinking agents that are incorporated in the polymer. In some embodiments, at least one of the one or more crosslinking agents is a di-functional crosslinking agent prior to incorporation in the polymer. In some embodiments, the di-functional crosslinking agent is selected from ethylene glycol dimethacrylate prior to being incorporated in the polymer or tetraethylene glycol dimethacrylate prior to being incorporated in the polymer. In some such embodiments, the polymer of the optic portion comprises incorporated ethylene glycol dimethacrylate, and the total weight of the ethylene glycol dimethacrylate ranges from 0.05 percent to 0.5 percent, and in some embodiments, from 0.08 percent to 0.25 percent or from 0.1 percent to 0.2 percent, based on the total weight of the dry polymer of the optic portion. In some embodiments, the at least one of the one or more crosslinking agents is a multi-functional crosslinking agent prior to incorporation in the polymer. In some such embodiments, the multi-functional crosslinking agent is selected from trimethylol propane trimethacrylate or trimethylol propane triacrylate prior to being incorporated in the polymer. the polymer of the optic portion comprises incorporated trimethylol propane trimethacrylate and/or trimethylol propane triacrylate, and the total combined weight of the trimethylol propane trimethacrylate and the trimethylol propane triacrylate ranges from 0.3 percent to 1.5 percent, and in some embodiments from 0.45 percent to 1.2 percent or from 0.5 to 1.0 percent, based on the total weight of the dry polymer of the optic portion.

In some embodiments, the polymer of the optic portion further includes water.

In some embodiments, the polymer of the optic portion further includes one or more ultraviolet absorbing compounds and/or one or more ultraviolet absorbing monomer that is incorporated in the polymer of optic portion.

In some embodiments, the polymer of the optic portion, comprises, consists of, or consists essentially of:

(a) an incorporated alkoxyalkyl methacrylate in an amount of from 87 percent to 98 percent by weight based on the total weight of the dry polymer;

(b) an incorporated hydroxyalkyl methacrylate in an amount of from 1.5 percent to 12 percent by weight based on the total weight of the dry polymer;

(c) an incorporated di-functional methacrylate and/or di-functional acrylate crosslinking agent in an amount ranging from 0.085 percent to 0.2 percent based on the total weight of the dry polymer;

(d) an incorporated multi-functional methacrylate and/or multifunctional acrylate crosslinking agent in an amount ranging from 0.4 percent to 1 percent based on the total weight of the dry polymer; and (e) optionally one or more additional ingredients selected from water, a ultraviolet absorbing compound or monomer, a colorant, or an antioxidant. In some such embodiments, the alkoxyalkyl methacrylate is ethoxyethyl methacrylate, the hydroxyalkyl methacrylate is 2-hydroxyethyl methacrylate, the di-functional methacrylate and/or acrylate crosslinking agent is ethylene glycol dimethacrylate, and the multi-functional methacrylate and/or acrylate crosslinking agent is trimethylol propane trimethacrylate.

In some embodiments, the glass transition temperature of the polymer of the optic portion is below about 35° C. whereas in other embodiments, the glass transition temperature is below about 30° C. or is below about 25° C. In some such embodiments, the glass transition temperature of the polymer of the optic portion is from about −25° C. to about 35° C., 30° C., or 25° C., and in other such embodiments is from about from about −5° C. to about 15° C., 20° C., or 25° C.

In some embodiments, the polymer of the optic portion has a refractive index of 1.40 or higher. In some such embodiments, the refractive index is 1.46 or higher whereas in other such embodiments the refractive index is 1.48 or higher.

In some embodiments, the polymer of the optic portion includes water, and the equilibrium water content is less than or about 5 percent based on the weight of the polymer after it is hydrated. In some such embodiments, the equilibrium water content ranges from 2 percent to 4.5 percent based on the weight of the polymer after it is hydrated, whereas in other embodiments this ranges from 2.3 to 4.2 percent.

In some embodiments, the polymers of the invention include substantially no aromatic polymer, and in some embodiments includes less than 2 percent, less than 1 percent, less than 0.5 percent, less than 0.25 percent, less than 0.1 percent, less than 0.05 percent, or less than 0.005 percent of any incorporated aromatic polymer based on the dry weight of the polymer.

In another aspect, the invention provides a polymer. The polymer comprises, consists of, or consists essentially of:
(a) one or more alkoxyalkyl methacrylate monomers and/or one or more alkoxyalkyl acrylate monomers that are incorporated in the polymer;
(b) one or more hydroxyalkyl methacrylate monomers and/or one or more hydroxyalkyl acrylate monomers that are incorporated in the polymer; and
(c) optionally, one or more crosslinking agents that are incorporated in the polymer. In some embodiments, the total combined weight of the one or more alkoxyalkyl methacrylate monomers and the one or more alkoxyalkyl acrylate monomers ranges from 75 percent to 99 percent based on the total weight of the dry polymer, and the total combined weight of the one or more hydroxyalkyl methacrylate monomers and the one or more hydroxyalkyl acrylate monomers ranges from 1 percent to 25 percent based on the total weight of the dry polymer.

In some embodiments of the polymer, the one or more alkoxyalkyl methacrylate monomers have the formula $R_1$—O—$R_2$-MA prior to being incorporated in the polymer, and the one or more alkoxyalkyl acrylate monomers have the formula, $R_3$—O—$R_4$-A prior to being incorporated in the polymer, wherein MA is methacrylate, A is acrylate, and $R_1$, $R_2$, $R_3$, and $R_4$ are independently selected from alkyl groups having from 1 to 5 carbon atoms. In some such embodiments, $R_1$ and $R_3$ have from 1 to 3 carbon atoms, and $R_2$ and $R_4$ have 2 or 3 carbon atoms. In some such embodiments, $R_1$ and $R_3$ have 2 carbon atoms, and $R_2$ and $R_4$ have 2 carbon atoms.

In some such embodiments, the polymer includes incorporated ethoxyethyl methacrylate. In some such embodiments, the polymer comprises incorporated ethoxyethyl methacrylate, and the total weight of the ethoxyethyl methacrylate ranges from 80 percent to 98 percent based on the total weight of the dry polymer. In some such embodiments, the polymer comprises incorporated ethoxyethyl methacrylate, and the total weight of the ethoxyethyl methacrylate ranges from 86 percent to 98 percent based on the total weight of the dry polymer.

In some embodiments of the polymer, the one or more hydroxyalkyl methacrylate monomers have the formula HO—$R_5$-MA prior to being incorporated in the polymer, and the one or more hydroxyalkyl acrylate monomers have the formula, HO—$R_6$-A prior to being incorporated in the polymer, wherein MA is methacrylate, A is acrylate, and $R_5$ and $R_6$ are independently selected from alkyl groups having from 1 to 4 carbon atoms. In some embodiments, $R_5$ and $R_6$ have from 2 to 3 carbon atoms. In some embodiments, $R_5$ and $R_6$ have 2 carbon atoms. In some such embodiments, the polymer includes incorporated ethoxyethyl methacrylate. In some embodiments, the total weight of the ethoxyethyl methacrylate ranges from 80 percent to 98 percent based on the total weight of the dry polymer. In some embodiments, the total weight of the ethoxyethyl methacrylate ranges from 86 percent to 98 percent based on the total weight of the dry polymer.

In some embodiments of the polymer, the one or more hydroxyalkyl methacrylate monomers have the formula HO—$R_5$-MA prior to being incorporated in the polymer, and the one or more hydroxyalkyl acrylate monomers have the formula, HO—$R_6$-A prior to being incorporated in the polymer, wherein MA is methacrylate, A is acrylate, and $R_5$ and $R_6$ are independently selected from alkyl groups having from 1 to 4 carbon atoms. In some such embodiments, $R_5$ and $R_6$ have from 2 to 3 carbon atoms, whereas in other embodiments, $R_5$ and $R_6$ have 2 carbon atoms. In some such embodiments, the polymer comprises incorporated 2-hydroxyethyl methacrylate. In some such embodiments, the total weight of the 2-hydroxyethyl methacrylate ranges from 1 percent to 20 percent based on the total weight of the dry polymer. In other such embodiments, the total weight of the 2-hydroxyethyl methacrylate ranges from 1 percent to 12 percent based on the total weight of the dry polymer.

In certain embodiments, the polymer includes the one or more crosslinking agents that are incorporated into the polymer. In some such embodiments, at least one of the one or more crosslinking agents is a di-functional crosslinking agent prior to incorporation in the polymer. In some such embodiments, the di-functional crosslinking agent is selected from ethylene glycol dimethacrylate prior to being incorporated in the polymer or tetraethylene glycol dimethacrylate prior to being incorporated in the polymer. In some embodiments, the polymer comprises incorporated ethylene glycol dimethacrylate, and the total weight of the ethylene glycol dimethacrylate ranges from 0.05 percent to 0.5 percent based on the total weight of the dry polymer. In other such embodiments, the total weight of the ethylene glycol dimethacrylate ranges from 0.08 percent to 0.25 percent based on the total weight of the dry polymer. In still other such embodiments, the total weight of the ethylene glycol dimethacrylate ranges from 0.1 percent to 0.2 percent based on the total weight of the dry polymer.

In other embodiments, the polymer includes the one or more crosslinking agents, and at least one of the one or more crosslinking agents is a multi-functional crosslinking agent prior to incorporation in the polymer. In some such embodiments, the multi-functional crosslinking agent is selected from trimethylol propane trimethacrylate or trimethylol propane triacrylate prior to being incorporated in the polymer. In some such embodiments, the polymer comprises incorporated trimethylol propane trimethacrylate and/or trimethylol propane triacrylate, and the total combined weight of the trimethylol propane trimethacrylate and the trimethylol propane triacrylate ranges from 0.3 percent to 1.5 percent based on the total weight of the dry polymer. In other such embodiments, the polymer comprises incorporated trimethylol propane trimethacrylate and/or trimethylol propane triacrylate, and the total combined weight of the trimethylol propane trimethacrylate and the trimethylol propane triacrylate ranges from 0.45 percent to 1.2 percent based on the total weight of the dry polymer. In still other such embodiments, the polymer comprises incorporated trimethylol propane trimethacrylate and/or trimethylol propane triacrylate, and the total combined weight of the trimethylol propane trimethacrylate and the trimethylol propane triacrylate ranges from 0.5 percent to 1.0 percent based on the total weight of the dry polymer.

In some embodiments, the polymer further includes water. In some such embodiments, the equilibrium water content is less than or about 5 percent based on the weight of the polymer after it is hydrated. In other such embodiments, the equilibrium water content ranges from 2 percent to 4.5 percent or from 2.3 to 4.2 percent based on the weight of the polymer after it is hydrated.

In other embodiments, the polymer of the further comprises one or more ultraviolet absorbing compounds and/or one or more ultraviolet absorbing monomer that is incorporated in the polymer of optic portion.

In still another embodiment, the polymer comprises, consists of, or consists essentially of:
(a) an incorporated alkoxyalkyl methacrylate in an amount of from 87 percent to 98 percent by weight based on the total weight of the dry polymer;
(b) an incorporated hydroxyalkyl methacrylate in an amount of from 1.5 percent to 12 percent by weight based on the total weight of the dry polymer;
(c) an incorporated di-functional methacrylate and/or di-functional acrylate crosslinking agent in an amount ranging from 0.085 percent to 0.2 percent based on the total weight of the dry polymer;
(d) an incorporated multi-functional methacrylate and/or multifunctional acrylate crosslinking agent in an amount ranging from 0.4 percent to 1 percent based on the total weight of the dry polymer; and
(e) optionally one or more additional ingredients selected from water, a ultraviolet absorbing compound or monomer, a colorant, or an antioxidant. In some such embodiments, the alkoxyalkyl methacrylate is ethoxyethyl methacrylate, the hydroxyalkyl methacrylate is 2-hydroxyethyl methacrylate, the di-functional methacrylate and/or acrylate crosslinking agent is ethylene glycol dimethacrylate, and the multi-functional methacrylate and/or acrylate crosslinking agent is trimethylol propane trimethacrylate.

In certain embodiments, the polymer includes substantially no aromatic polymer.

In another aspect, the invention provides a method for manufacturing a polymer. The method includes:
(a) polymerizing a mixture to form the polymer, wherein the mixture comprises, consists of, or consists essentially of:
(i) one or more alkoxyalkyl methacrylate monomers and/or one or more alkoxyalkyl acrylate monomers;
(ii) one or more hydroxyalkyl methacrylate monomers and/or one or more hydroxyalkyl acrylate monomers;
(iii) optionally, one or more crosslinking agents; and
(iv) optionally, one or more initiator.

In some embodiments, the total combined weight of the one or more alkoxyalkyl methacrylate monomers and the one or more alkoxyalkyl acrylate monomers in the mixture ranges from 75 percent to 99 percent based on the total combined weight of the one or more alkoxyalkyl methacrylate monomers, the one or more alkoxyalkyl acrylate monomers, the one or more hydroxyalkyl methacrylate monomers, the one or more hydroxyalkyl acrylate monomers, and the one or more crosslinking agents in the mixture, and the total combined weight of the one or more hydroxyalkyl methacrylate monomers and the one or more hydroxyalkyl acrylate monomers in the mixture ranges from 1 percent to 25 percent based on the total combined weight of the one or more alkoxyalkyl methacrylate monomers, the one or more alkoxyalkyl acrylate monomers, the one or more hydroxyalkyl methacrylate monomers, the one or more hydroxyalkyl acrylate monomers, and the one or more crosslinking agents in the mixture.

In some embodiments of the method for manufacturing a polymer, the mixture is polymerized in a mold. In some embodiments, the method further includes forming an optic portion of an intraocular lens from the polymer. In some such embodiments, the method further includes forming an intraocular lens from the optic portion. In some embodiments, the method for manufacturing a polymer further includes forming an intraocular lens from the polymer.

In some embodiments of the method for manufacturing a polymer, the one or more alkoxyalkyl methacrylate monomers have the formula $R_1$—O—$R_2$-MA, and the one or more alkoxyalkyl acrylate monomers have the formula, $R_3$—O—$R_4$-A, wherein MA is methacrylate, A is acrylate, and $R_1$, $R_2$, $R_3$, and $R_4$ are independently selected from alkyl groups having from 1 to 5 carbon atoms. In some such embodiments, $R_1$ and $R_3$ have from 1 to 3 carbon atoms, and $R_2$ and $R_4$ have 2 or 3 carbon atoms. In some such embodiments, $R_1$ and $R_3$ have 2 carbon atoms, and $R_2$ and $R_4$ have 2 carbon atoms. In some embodiments, the mixture comprises ethoxyethyl methacrylate. In some such embodiments, the mixture comprises ethoxyethyl methacrylate, and the total weight of the ethoxyethyl methacrylate in the mixture ranges from 80 percent to 98 percent based on the total combined weight of the one or more alkoxyalkyl methacrylate monomers, the one or more alkoxyalkyl acrylate monomers, the one or more hydroxyalkyl methacrylate monomers, the one or more hydroxyalkyl acrylate monomers, and the one or more crosslinking agents in the mixture. In still other such embodiments, the mixture comprises ethoxyethyl methacrylate, and the total weight of the ethoxyethyl methacrylate in the mixture ranges from 86 percent to 98 percent based on the total combined weight of the one or more alkoxyalkyl methacrylate monomers, the one or more alkoxyalkyl acrylate monomers, the one or more hydroxyalkyl methacrylate monomers, the one or more hydroxyalkyl acrylate monomers, and the one or more crosslinking agents in the mixture.

In some embodiments of the method for manufacturing a polymer, the one or more hydroxyalkyl methacrylate monomers have the formula HO—$R_5$-MA, and the one or more hydroxyalkyl acrylate monomers have the formula, HO—$R_6$-A, wherein MA is methacrylate, A is acrylate, and $R_5$ and $R_6$ are independently selected from alkyl groups having from 1 to 4 carbon atoms. In some such embodiments, $R_5$ and $R_6$ have from 2 to 3 carbon atoms. In still other such embodiments, $R_5$ and $R_6$ have 2 carbon atoms. In some such embodiments, the mixture comprises 2-hydroxyethyl methacrylate. In still other such embodiments, the mixture comprises 2-hydroxyethyl methacrylate, and the total combined weight of the 2-hydroxyethyl methacrylate in the mixture ranges from 1 percent to 20 percent based on the total combined weight of the one or more alkoxyalkyl methacrylate monomers, the one or more alkoxyalkyl acrylate monomers, the one or more hydroxyalkyl methacrylate monomers, the one or more hydroxyalkyl acrylate monomers, and the one or more crosslinking agents in the mixture. In some such embodiments, the mixture comprises 2-hydroxyethyl methacrylate, and the total weight of the 2-hydroxyethyl methacrylate in the mixture ranges from 1 percent to 12 percent based on the total combined weight of the one or more alkoxyalkyl methacrylate monomers, the one or more alkoxyalkyl acrylate monomers, the one or more hydroxyalkyl methacrylate monomers, the one or more hydroxyalkyl acrylate monomers, and the one or more crosslinking agents in the mixture.

In some embodiments of the method for manufacturing a polymer, the mixture comprises, the one or more crosslinking agents. In some such embodiments, at least one of the one or more crosslinking agents is a di-functional crosslinking agent. In some such embodiments, the di-functional crosslinking agent is selected from ethylene glycol dimethacrylate or tetraethylene glycol dimethacrylate. In some such embodiments, the mixture comprises ethylene glycol dimethacrylate, and the total weight of the ethylene glycol dimethacrylate in the mixture ranges from 0.05 percent to 0.5 percent based on the total combined weight of the one or more alkoxyalkyl methacrylate monomers, the one or more alkoxyalkyl acrylate monomers, the one or more hydroxyalkyl methacrylate monomers, the one or more hydroxyalkyl acrylate monomers, and the one or more crosslinking agents in the mixture. In some such embodiments, the mixture comprises ethylene glycol dimethacrylate, and the total weight of the ethylene glycol dimethacrylate in the mixture ranges from 0.08 percent to 0.25 percent based on the total combined weight of the one or more alkoxyalkyl methacrylate monomers, the one or more alkoxyalkyl acrylate monomers, the one or more hydroxyalkyl methacrylate monomers, the one or more hydroxyalkyl acrylate monomers, and the one or more crosslinking agents in the mixture. In still other such embodiments, the mixture comprises ethylene glycol dimethacrylate, and the total weight of the ethylene glycol dimethacrylate ranges from 0.1 percent to 0.2 percent based on the total combined weight of the one or more alkoxyalkyl methacrylate monomers, the one or more alkoxyalkyl acrylate monomers, the one or more hydroxyalkyl methacrylate monomers, the one or more hydroxyalkyl acrylate monomers, and the one or more crosslinking agents in the mixture. In some embodiments in which the mixture comprising one or more crosslinking agents, at least one of the one or more crosslinking agents is a multi-functional crosslinking agent. In some such embodiments, the multi-functional crosslinking agent is selected from trimethylol propane trimethacrylate or trimethylol propane triacrylate. In some other such embodiments, the mixture comprises trimethylol propane trimethacrylate and/or trimethylol propane triacrylate, and the total combined weight of the trimethylol propane trimethacrylate and the trimethylol propane triacrylate in the mixture ranges from 0.3 percent to 1.5 percent based on the total combined weight of the one or more alkoxyalkyl methacrylate monomers, the one or more alkoxyalkyl acrylate monomers, the one or more hydroxyalkyl methacrylate monomers, the one or more hydroxyalkyl acrylate monomers, and the one or more crosslinking agents in the mixture. In certain such embodiments, the mixture comprises trimethylol propane trimethacrylate and/or trimethylol propane triacrylate, and the total combined weight of the trimethylol propane trimethacrylate and the trimethylol propane triacrylate in the mixture ranges from 0.45 percent to 1.2 percent based on the total combined weight of the one or more alkoxyalkyl methacrylate monomers, the one or more alkoxyalkyl acrylate monomers, the one or more hydroxyalkyl methacrylate monomers, the one or more hydroxyalkyl acrylate monomers, and the one or more crosslinking agents in the mixture. In still other such embodiments, the mixture comprises trimethylol propane trimethacrylate and/or trimethylol propane triacrylate, and the total combined weight of the trimethylol propane trimethacrylate and the trimethylol propane triacrylate in the mixture ranges from 0.5 percent to 1.0 percent based on the total combined weight of the one or more alkoxyalkyl methacrylate monomers, the one or more alkoxyalkyl acrylate monomers, the one or more hydroxyalkyl methacrylate monomers, the one or more hydroxyalkyl acrylate monomers, and the one or more crosslinking agents in the mixture.

In some embodiments of the method for manufacturing a polymer, the mixture further comprises one or more ultraviolet absorbing compounds and/or one or more ultraviolet absorbing monomer.

In some embodiments of the method for manufacturing a polymer, the mixture comprises, consists of, or consists essentially of:

(a) an alkoxyalkyl methacrylate, wherein the alkoxyalkyl methacrylate is present in the mixture in an amount of from 87 percent to 98 percent by weight based on the total combined weight of the one or more alkoxyalkyl methacrylate monomers, the one or more alkoxyalkyl acrylate monomers, the one or more hydroxyalkyl methacrylate monomers, the one or more hydroxyalkyl acrylate monomers, and the one or more crosslinking agents in the mixture;

(b) a hydroxyalkyl methacrylate, wherein the hydroxyalkyl methacrylate is present in the mixture in an amount of from 1.5 percent to 12 percent by weight based on the total combined weight of the one or more alkoxyalkyl methacrylate monomers, the one or more alkoxyalkyl acrylate monomers, the one or more hydroxyalkyl methacrylate monomers, the one or more hydroxyalkyl acrylate monomers, and the one or more crosslinking agents in the mixture;

(c) a di-functional methacrylate and/or di-functional acrylate crosslinking agent, wherein the combined weight of the di-functional methacrylate and/or the di-functional acrylate crosslinking agent in the mixture ranges from 0.085 percent to 0.2 percent based on the total combined weight of the one or more alkoxyalkyl methacrylate monomers, the one or more alkoxyalkyl acrylate monomers, the one or more hydroxyalkyl methacrylate monomers, the one or more hydroxyalkyl acrylate monomers, and the one or more crosslinking agents in the mixture;

(d) a multi-functional methacrylate and/or multifunctional acrylate crosslinking agent, wherein the combined weight of the multi-functional methacrylate and/or the multi-functional acrylate crosslinking agent in the mixture ranges from 0.4 percent to 1 percent based on the total combined weight of the one or more alkoxyalkyl methacrylate monomers, the one or more alkoxyalkyl acrylate monomers, the one or more hydroxyalkyl methacrylate monomers, the one or more hydroxyalkyl acrylate monomers, and the one or more crosslinking agents in the mixture; and (e) optionally one or more additional ingredients selected from an initiator, an ultraviolet absorbing compound or monomer, a colorant, or an antioxidant. In some such embodiments, the alkoxyalkyl methacrylate is ethoxyethyl methacrylate, the hydroxyalkyl methacrylate is 2-hydroxyethyl methacrylate, the di-functional methacrylate and/or acrylate crosslinking agent is ethylene glycol dimethacrylate, and the multi-functional methacrylate and/or acrylate crosslinking agent is trimethylol propane trimethacrylate.

In some embodiments of the method for manufacturing a polymer, the equilibrium water content is less than or about 5 percent based on the weight of the polymer after it is hydrated. In some such embodiments, the equilibrium water content ranges from 2 percent to 4.5 percent based on the weight of the polymer after it is hydrated. In still other such embodiments, the equilibrium water content ranges from 2.3 percent to 4.2 percent based on the weight of the polymer after it is hydrated.

In some embodiments of the method for manufacturing a polymer, the mixture contains substantially no aromatic polymer. In still other such embodiments, the mixture comprises less than 2 percent by weight of any aromatic component.

In some embodiments of the method for manufacturing a polymer, the method further includes attaching one or more haptic portions to an optic portion formed from the polymer.

The present invention also provides a method for modifying, correcting or improving an individual's eyesight that includes inserting any of the present intraocular lenses into an eye of a subject. This method can also include folding the intraocular lens prior to inserting the intraocular lens into the eye and allowing the intraocular lens to unfold after it is inserted into the eye. These methods can also include removing a lens, either natural or artificial, from the eye of the subject prior to inserting the intraocular lens.

Further objects, features, and advantages of the present invention will become apparent from the following detailed description and drawings.

DETAILED DESCRIPTION OF THE PREFERRED EMBODIMENTS

Figure 1A:
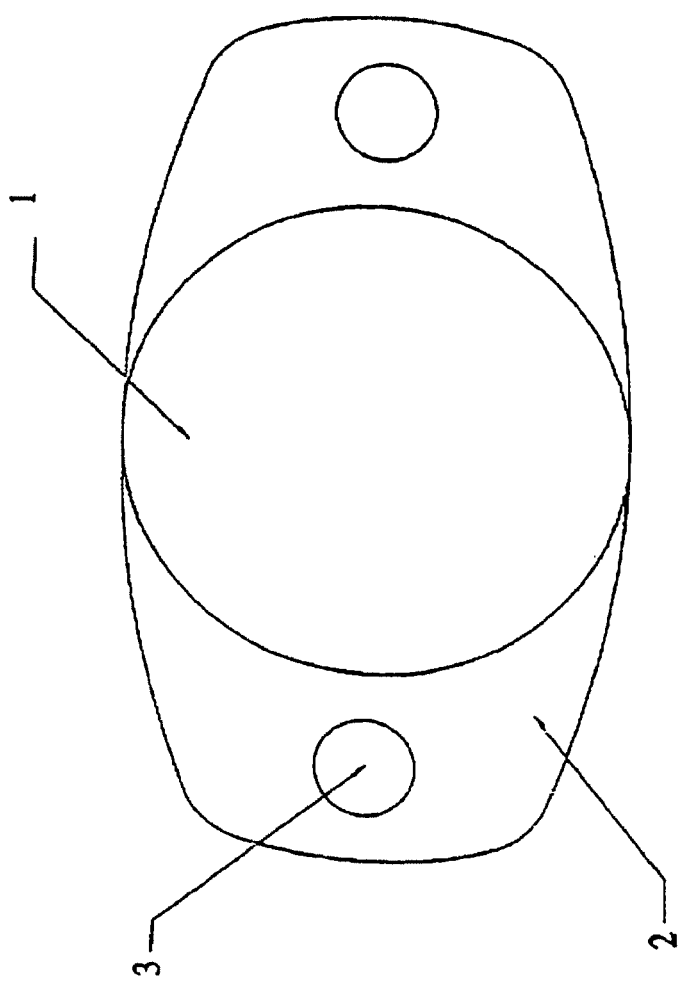
FIG. 1A is a top view of an intraocular lens having a plate-shaped haptic.

The present invention provides polymer compositions that are particularly useful for manufacturing optic portions intraocular lenses and intraocular lenses. A polymer for the purposes of the present invention means a polymer formed from one or more different polymerizable monomers and may include crosslinkers and other additives as described herein. These polymers have as their primary components, i.e. the primary monomer present in the polymer by weight, a combination of one or more alkoxyalkyl methacrylate monomers and/or one or more alkoxyalkyl acrylate monomers. For purposes of the present invention, all of the one or more alkoxyalkyl methacrylate monomers, which can be the same or different, and/or the one or more alkoxyalkyl acrylate monomers, which can also be the same or different, are considered as single component of the present polymers.

Alkoxyalkyl methacrylate monomers can be represented by the formula $R_1$—O—$R_2$-MA where $R_1$ and $R_2$ are alkyl groups and "MA" is methacrylate. Alkoxyalkyl acrylate monomers can be represented by the formula $R_3$—O—$R_4$-A where $R_3$ and $R_4$ are alkyl groups and "A" is acrylate. Both alkoxyalkyl methacrylates and alkoxyalkyl acrylates are ester-containing monomer compounds as will be recognized by those skilled in the art. In some embodiments, $R_1$ to $R_4$ can be independently selected from alkyl groups having 1 to 5 carbon atoms and in some embodiments 1, 2, 3, 4, or 5 carbon atoms. With respect to $R_2$, it will be understood that the alkyl group is bonded to the O of the $R_1$—O group and is also bonded to the O atom of the MA group. Similarly, with respect to $R_4$, it will be understood that the alkyl group is bonded to the O of the $R_3$—O group and is also bonded to the O atom of the A group. Alkyl groups that may be used in accordance with the invention include straight chain alkyl groups, including but not limited to methyl, ethyl, propyl, butyl, and pentyl groups. Alkyl groups may also include branched chain isomers of straight chain alkyl groups including, but not limited to, the following, which are provided by way of example only: —$CH(CH_3)_2$, —$CH(CH_3)(CH_2CH_3)$, —$CH(CH_2CH_3)_2$, —$C(CH_3)_3$, and the like. In some embodiments, the alkoxyalkyl methacrylate or alkoxyalkyl acrylate is selected where $R_1$ to $R_4$ have 1, 2, 3, or 4 carbon atoms. Examples of some specific alkoxyalkyl methacrylate and alkoxyalkyl acrylate monomers useful for forming the polymers of the invention include, but are not limited to, methoxyethyl methacrylate, ethoxyethyl methacrylate, propoxyethyl methacrylate, butoxymethyl methacrylate, methoxypropyl methacrylate, ethoxypropyl methacrylate, propoxypropyl methacrylate, butoxypropyl methacrylate, methoxybutyl methacrylate, ethoxybutyl methacrylate, propoxybutyl methacrylate, butoxybutyl methacrylate, methoxyethyl acrylate, ethoxyethyl acrylate, propoxyethyl acrylate, butoxymethyl acrylate, methoxypropyl acrylate, ethoxypropyl acrylate, propoxypropyl acrylate, butoxypropyl acrylate, methoxybutyl acrylate, ethoxybutyl acrylate, propoxybutyl acrylate, and butoxybutyl acrylate. In some embodiments, the polymer includes ethoxyethyl methacrylate (EOEMA).

The present polymers also include one or more hydrophilic monomer. Examples of such hydrophilic monomers include hydroxyalkyl methacrylates and hydroxyalkyl acrylates. Hydroxyalkyl methacrylates may be represented by the formula HO—$R_5$-MA where $R_5$ is an alkyl group having 1 to 4 carbon atoms and "MA" is methacrylate. Hydroxyalkyl acrylates may be represented by the formula HO—$R_6$-A where $R_6$ is an alkyl group having from 1 to 4 carbon atoms and "A" is acrylate. With respect to $R_5$, it will be understood that the alkyl group is bonded to the O of the HO group and is also bonded to the O atom of the MA group. Similarly, with respect to $R_6$, it will be understood that the alkyl group is bonded to the O of the HO group and is also bonded to the O atom of the A group. Examples of hydroxyalkyl methacrylates and hydroxyalkyl acrylates include, but not limited to 2-hydroxyethyl methacrylate, 3-hydroxypropyl methacrylate, 2-hydroxypropyl methacrylate, 2-hydroxybutyl methacrylate, 3-hydroxybutyl methacrylate, 4-hydroxybutyl methacrylate, 2-hydroxyethyl acrylate, 3-hydroxypropyl acrylate, 2-hydroxypropyl acrylate, 2-hydroxybutyl acrylate, 3-hydroxybutyl acrylate, and 4-hydroxybutyl acrylate. In some embodiments, the polymer includes 2-hydroxyethyl methacrylate (HEMA).

The polymers of the present invention include the alkoxyalkyl methacrylate and/or alkoxyalkyl acrylate monomers as the major component and the hydrophilic monomer(s) as the minor component.

As used herein, the term "polymer" refers to a composition that is formed by polymerizing one or more different monomers. The term "polymer" thus includes "homopolymers" formed from only one type of monomer, "copolymers" which are formed from two or more different monomers, "terpolymers" formed from at least three different monomers, and any polymer that is formed from at least one type of monomer and may be formed from one, two, three, four, or more different monomers.

Other monomers may be present in the polymers of the present invention including, but not limited to, alkoxyalkoxyalkyl methacrylates such as, but not limited to, ethoxyethoxyethyl methacrylate; alkoxyalkoxyalkyl acrylates, such as, but not limited to ethoxyethoxyethyl acrylate; alkyl methacrylate monomers; and combinations thereof with specific examples of alkyl methacrylate monomers being $C_1$ alkyl to $C_{15}$ alkyl methacrylate monomers such as, but not limited to, methyl methacrylate, ethyl methacrylate, propyl methacrylate, butyl methacrylate, hexyl methacrylate, lauryl methacrylate, and combinations thereof. Some embodiments of the invention do not include any alkoxyalkoxyalkyl methacrylate or any alkoxyalkoxyalkyl methacrylate.

In the present polymers, the total quantity of the one or more alkoxyalkyl methacrylate and/or the one or more alkoxyalkyl acrylate monomers will make up the majority of the polymer. For example, in some embodiments, the total quantity of the combined amounts of any alkoxyalkyl methacrylate and/or alkoxyalkyl acrylate monomer(s) is greater than about 80 percent by weight based on the total weight of the polymer. In some such embodiments, the total quantity of the combined amounts of any alkoxyalkyl methacrylate and/or alkoxyalkyl acrylate monomer(s) is greater than about 85 percent, greater than about 90 percent, or greater than about 95 percent by weight based on the total weight of the polymer. In still other embodiments, the total quantity of the combined amounts of any alkoxyalkyl methacrylate and/or alkoxyalkyl acrylate monomer(s) is greater than about 96, 97, or 98 percent by weight based on the total weight of the polymer.

The present polymers can also include various other components that improve the characteristics of the polymer. Non-limiting examples of other components include one or more ultraviolet absorbing compounds, one or more crosslinking agents, such as, but not limited to, incorporated ethylene glycol dimethacrylate (EGDMA), incorporated tetraethylene glycol dimethacrylate (TEGDMA), incorporated trimethylol propane trimethacrylate (TMPTMA) or the analogous triacrylate, one or more colorants, and combinations thereof. Those skilled in the art will recognize that various known cross-linking agents may be used in the polymers and methods in accordance with the invention.

When a polymer is said to include a monomer such as ethoxyethyl methacrylate, it will be understood that this means that the ethoxyethyl methacrylate monomer has been reacted and incorporated into the polymer.

One exemplary polymeric composition contains about 87 percent to about 99 percent of an alkoxyalkyl methacrylate and about 1 percent to about 13 percent of a hydroxyalkyl methacrylate, with the balance of the polymer being made up of other components, such as UV absorbers, initiation agents and/or crosslinking agents. Another exemplary composition contains about 88 percent to about 98 percent of an alkoxyalkyl methacrylate and about 2 percent to about 12 percent of a hydroxyalkyl methacrylate with the balance of the polymer again being made up of other components. Another exemplary composition contains about 90 percent to about 98 percent of an alkoxyalkyl methacrylate and about 2 percent to about 10 percent of a hydroxyalkyl methacrylate with the balance of the polymer again being made up of other components. Still other exemplary compositions contain about 92 percent to about 96 percent of an alkoxyalkyl methacrylate and about 4 percent to about 8 percent of a hydroxyalkyl methacrylate with the balance of the polymer again being made up of other components. In some of these compositions, the alkoxyalkyl methacrylate may be ethoxyethyl methacrylate. In still other such compositions, the hydroxyalkyl methacrylate is 2-hydroxyethyl methacrylate. As can be seen from these exemplary compositions, the present intraocular lens can have a range of material components and still have the desired characteristics. The polymer compositions of the present invention generally include one or more crosslinking agent. In some embodiments, the compositions includes one or more crosslinker with two polymerizable functionalities (a di-functional crosslinking agent). Examples of such crosslinking agents include, but are not limited to ethylene glycol dimethacrylate (EGDMA) and tetraethylene glycol dimethacrylate (TEGDMA). Some embodiments also include a crosslinking agent with three or more polymerizable functionalities (a multi-functional crosslinking agent). An example of a multi-functional crosslinking agent includes, but is not limited to, trimethylol propane trimethacrylate (TMPTMA). The analogous acrylate crosslinking agents, for example, ethylene glycol diacrylate, tetraethylene glycol diacrylate, and trimethylol propane triacrylate, may also be utilized in accordance with the invention in place of any of their methacrylate analogs or in combination with the methacrylate analogs. Some embodiments include two or more di-functional crosslinking agents. Still other embodiments include both a di-functional crosslinking agent and a multi-functional crosslinking agent. Therefore, in some embodiments, the polymer compositions include EGDMA and TMPTMA. In some such embodiments, the amount of EGDMA ranges from about 0.05 to about 0.5 or about 0.4 percent by weight based on the weight of the dry polymer and the amount of the TMPTMA ranges from about 0.3 to about 1.5 percent by weight based on the weight of the dry polymer. In some such embodiments, the amount of EGDMA ranges from about 0.08 to about 0.25 percent by weight based on the weight of the dry polymer and the amount of the TMPTMA ranges from about 0.45 to about 1.2 percent by weight based on the weight of the dry polymer. In still other such embodiments, the amount of EGDMA ranges from about 0.1 to about 0.2 percent by weight based on the weight of the dry polymer and the amount of the TMPTMA ranges from about 0.5 to about 1.0 percent by weight based on the weight of the dry polymer. In some of embodiments, the polymer compositions of the present invention consist of or consist essentially of a polymer formed from an alkoxyalkyl methacrylate, a hydroxyalkyl methacrylate, and one or more crosslinking agent. In some such embodiments, the polymer is formed from a monomers consisting of ethoxyethyl methacrylate, 2-hydroxyethyl methacrylate, EGDMA, and TMPTMA. In some such embodiments, the ratio of the EGDMA to the TMPTMA ranges from 1:4 to 1:6 and in some embodiments is about 1:5. In some such embodiments, the ratio of the EOEMA to HEMA used to make the polymer ranges from 88:12 to 98:2. In embodiments, a polymer of the invention comprises, consists essentially of, or consists of:

(a) An incorporated alkoxyalkyl methacrylate such as EOEMA in an amount of from 87 to 98 percent;

(b) An incorporated hydroxyalkyl methacrylate such as HEMA in an amount of from 1.5 to 12 percent;

(c) An incorporated di-functional methacrylate or acrylate crosslinking agent such as EGDMA in an amount ranging from 0.085 to 0.2 percent;

(d) An incorporated multi-functional methacrylate or acrylate crosslinking agent such as TMPTMA in an amount ranging from 0.4 to 1 percent; and (e) One or more optional other ingredients such as water, one or more UV absorbing compound or monomer, a colorant, and an antioxidant.

In most embodiments, the present polymers will contain no, or substantially no, monomers that have aromatic constituents. Previously, aromatic monomers have been added to polymers in order to increase the refractive index of the polymer so as to make the polymer more suitable for lens formation. However, aromatic monomers also increase the stiffness of the resulting polymer making any resulting lens made from the polymer more difficult to manipulate or fold without damaging the lens. The present polymers overcome this problem by balancing the physical characteristics of the polymer used to make the lens. Accordingly, in some embodiments 10 percent, 5 percent, 2 percent, 1 percent, 0.1 percent or less of the monomers used to make the present polymers will have aromatic constituents.

The polymers of the present invention generally have a water content of less than or about 5 percent based on the weight of the polymer after it is fully equilibrated in water. In some embodiments, the polymers have a water content at equilibrium that ranges from at or about 2 percent to at or about 4.5 percent based on the weight of the polymer after it is fully equilibrated in water. In other embodiments, the water content ranges from about 2.3 percent to about 4.2 percent by weight of the polymer after it is fully equilibrated with water.

The polymers of the present invention possess superior mechanical and optical properties over other materials used to make IOLs. The combination of a hydrophilic monomer such as a hydroxyalkyl methacrylate with a hydrophobic monomer such as an alkoxyalkyl methacrylate provides materials with higher levels of water than is possible without incorporation of the hydrophilic monomer. Therefore, the unique combination of materials provides polymers compositions that may be used to prepare IOLs with improved folding and unfolding properties as compared with acrylic rubbers. At the same time, the higher water levels of the polymers of the invention provides increased hydrophilicity at the lens surface thus providing improved biocompatibility.

The present polymers can be designed to have a wide range of physical characteristics. In some instances, the present polymers can be designed to have glass transition temperatures below at or about 35° C., below at or about 30° C., below at or about 25° C., such as from at or about −25° C. to at or about 35° C., 30° C., or 25° C., from about −5° C. to about 15° C., 20° C., or about 25° C. or from at or about 0° C. to at or about 15° C. One skilled in the art will recognize that the lower the glass transition temperature the more rubbery the polymer. As the present polymers have been designed to be used as intraocular lenses, they also typically have a high refractive index, which is generally above about 1.40. Some of the present polymers can have a refractive index of 1.48 or higher. Because the present polymers are hydrophobic, they can also have equilibrium water contents that are about 5 percent or less, for example 3 percent, 2 percent, 1 percent or less. Due to their low water contents, the present polymers are generally not considered hydrogels and may be considered as hydrophobic. Generally, the present lenses also have advantageous properties compared to prior lenses because they have a comparable or higher refractive index than lenses containing silicone or p-hydroxyethyl methacrylate and are more flexible, e.g., foldable, than hydrophobic lenses that include aromatic monomers to increase the refractive index of the resulting polymer.

The present invention also provides intraocular lenses made at least partially from the present polymers. Such intraocular lenses include an optic portion and one or more haptic portions. Typically, the polymers of the invention will make up part or all of the optic portion of the intraocular lens. In some embodiments, the optic portion of the lens will have a core made from one of the present polymers surrounded by different polymer or material. Lenses in which the optic portion is made up of at least partially of one of the present polymers will usually also have a haptic portion. The haptic portion can also be made of polymer of the invention or can be made of a different material, for example another polymer.

In some embodiments, the present intraocular lens is a one-piece lens having a soft, foldable central optic region and an outer peripheral region (haptic-region) in which both regions are made of the same polymer. In other embodiments, the optic and haptic regions can be formed from different types of polymers or materials, if desired. Some lenses can also have haptic portions that are made up of different materials, for example where one or more haptic portions is made from the same material as the optic portion and other haptic portions are made of materials other than a polymer of the invention. Multicomponent lenses can be made by embedding one material in the other, concurrent extrusion processes, solidifying the hard material about the soft material, or forming an interpenetrating network of the rigid component into a preformed hydrophobic core. In instances where one or more haptic portions are made from a different material than the optic portion of the lens, the haptic portion can be attached to the optic portion in any manner known in the art, such as by drilling a hole or holes in the optic portion and inserting the haptic portion.

The polymers of the present invention have been designed so that they are capable of being folded so that the intraocular lens can be inserted into the eye of an individual through a small incision. The haptic portion of the lens provides the required support for the lens in the eye after insertion and unfolding of the lens and tends to help stabilize the position of the lens after insertion and the closure of the incision. The shape of the haptic portion design is not particularly limited and can be any desired configuration, for example, either a plate type or graduated thickness spiral filaments, also known as a C-loop design.

Figure 1B:
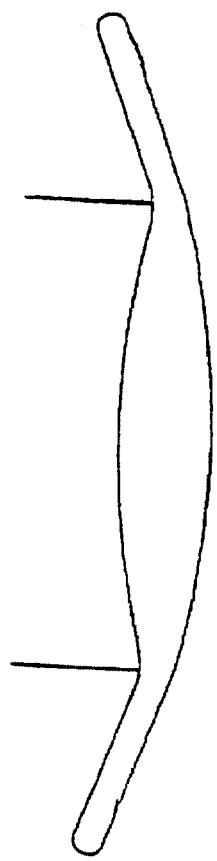
FIG. 1B is a side view of the intraocular lens having a plate-shaped haptic shown in FIG. 1A.
Figure 2A:
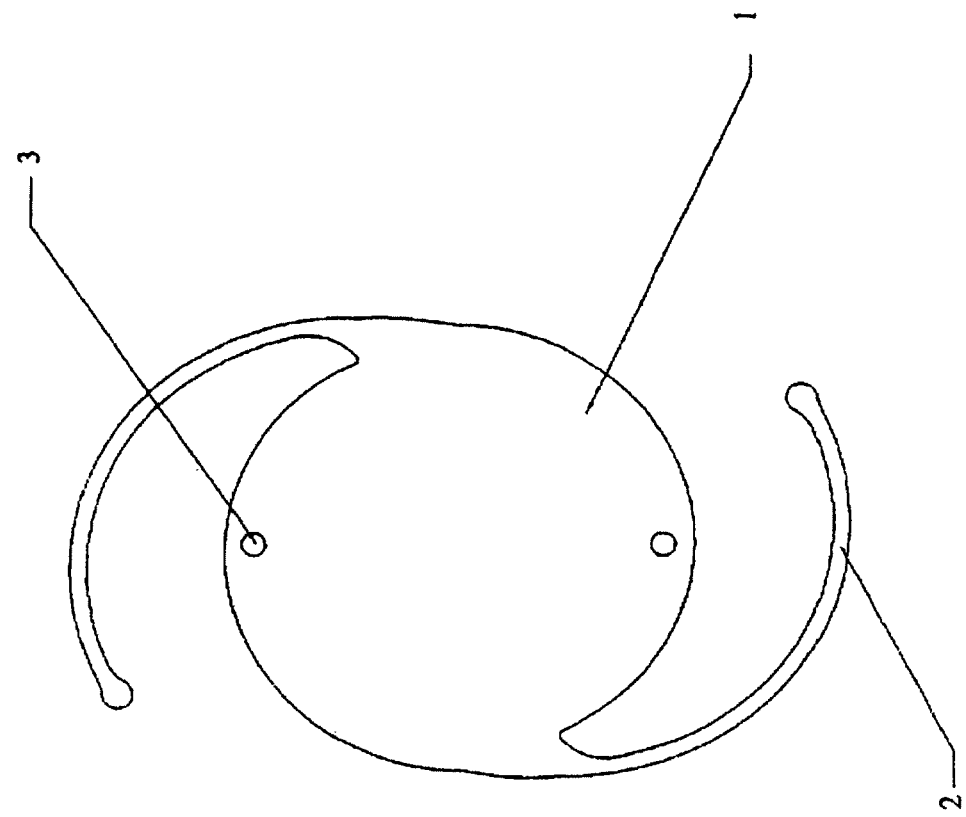
FIG. 2A is a top view of an intraocular lens having a C-shaped haptic.
Figure 2B:
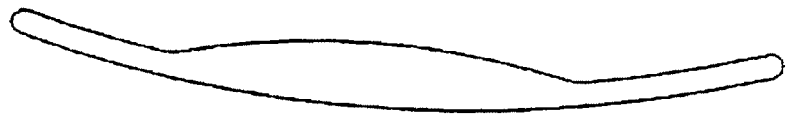
FIG. 2B is a side view of the intraocular lens having a C-shaped haptic shown in FIG. 2A.
Figure 3:
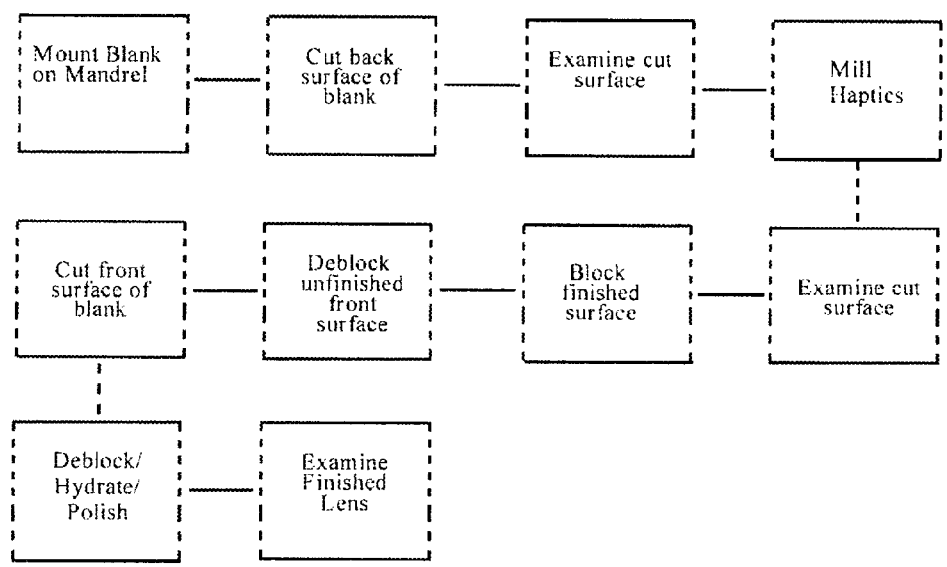
FIG. 3 is a general description of a stepwise process for forming the blanks into intraocular lenses according to some embodiments of the present disclosure.

FIGS. 1A, 1B, 2A, and 2B illustrate examples of intraocular lenses in accordance with the present invention. The figures are for illustrative purposes only and do not limit the scope of the invention. For instance, the intraocular lens can be any type of intraocular lens. In the figures, 1 is the optic portion of the lens, 2 is the haptic portion, and 3 is a positioning hole. One skilled in the art of intraocular lenses understands the functions of these portions of the intraocular lens.

The optic portion 1 can be approximately 6 mm in diameter prior to hydration. The 6 mm diameter is fairly standard in the art, and is generally chosen to cover the pupil in its fully dilated state under naturally occurring conditions. However, other sizes are possible and the present invention is not limited to any particular diameter or size of intraocular lens. Furthermore, it is not necessary that the lens optic portion be circular; it could also be oval, square, or any other shape as desired.

The intraocular lens can further include one or more non-optical haptic components 2 extending away from the outermost peripheral surface of the optic portion. The haptic components can be of any desired shape, for example, graduated spiral filaments or flat plate sections and are used to support the lens within the posterior chamber of the eye. Lenses having any desired design configuration can be fabricated. Further, although two types of haptic designs are shown in the figures, the haptics can have configurations other than those illustrated. Should the intraocular lens include other components besides the optical and haptic portions, such other portions can be made of a polymer as are the haptic and optic portions, or if desired, another material.

The intraocular lenses of the invention may be inserted into the eye in known manners. For example, the intraocular lens may be folded prior to insertion into the eye by small, thin forceps of the type typically used by ophthalmic surgeons. After the lens is in the targeted location, it is released to unfold. As is well known in the art, typically the lens that is to be replaced is removed prior to insertion of the intraocular lens. The intraocular lens of the present invention can be made of a generally physiologically inert soft polymeric material that is capable of providing a clear, transparent, refractive lens body even after folding and unfolding. In some embodiments, the foldable intraocular lens of the present invention can be inserted into any eye by injection whereby the mechanically compliant material is folded and forced through a small tube such as a 1 mm to 3 mm inner diameter tube.

The polymers of the invention can be prepared using conventional polymerization techniques known to those in the field of polymer chemistry. Crosslinkers, also referred to as crosslinking agents, may be employed in the polymerization reaction. For example, any suitable crosslinking di-functional, multi-functional monomer, or combination of these can be used in effective amounts to give the desired crosslinking density. For example, in a concentration range of 0.4 to about 4 percent, such as about 0.4 to about 3 percent, or in some embodiments from 0.5 to 1.5 percent by weight, based on the weight of the polymer. Examples of suitable crosslinking agents include di-olefinic compounds such as ethylene glycol dimethacrylate (EGDMA) and tetraethylene glycol dimethacrylate (TEGDMA) and other cross-linking agents such as trimethylol propane trimethacrylate (TMPTMA) which include three or more olefinic polymerizable functionalities. Generally, crosslinkers help to enhance the resulting polymer's dimensional stability.

Also, if desired an initiator can be used in the polymerization. Any initiator commonly used in the art, such as azo derivatives, like 2,2-azobis(2,4-dimethylvaleronitrile) and propanenitrile,2-methyl,2,2'-azobis, can be used. The initiator is used in an amount effective for initiation purposes, and is generally present from about 0.01 to 1.0 percent by weight, based on the weight of the polymer.

The polymers of the present invention can also include additional monomers, such as, but not limited to, monomers that impart UV absorption to the polymer. UV absorbing monomers are typically aromatic compounds with olefinic functionality. The advantageous ultraviolet (UV) absorbing compounds can be added prior to polymerization for incorporation into the resultant polymer, as is well known in the art. The UV absorber should preferably be capable of polymerization into the lens matrix so as to be stable under physiological conditions. Any monomer copolymerizable with the described monomers can optionally be used, so long as such does not materially, adversely effect the basic characteristics of the intraocular lens. Examples of useful additional monomers that can used are described in U.S. Pat. No. 5,326,506, hereby incorporated by reference, directed to a composite intraocular lens. Such optional additional monomers, preferably are present in a total amount of not more than 10 weight percent, generally less than 5 weight percent, based on the total weight of the polymer.

As described above, it may be useful to add crosslinking agents such as EGDMA, TEGDMA, or TMPTA, for example, to enhance the resulting polymer's dimensional stability. It may also be advantageous to add ultraviolet (UV) absorbing compounds with the lens monomers prior to polymerization for incorporation into the resultant polymer. The UV absorber should preferably be capable of polymerization into the lens matrix so as to resist extraction under physiologic conditions. The UV-absorbing monomer can be present in an amount effective to give the desired UV-absorbing properties, generally less than 4 percent by weight of the polymer, such as from 0.01 to about 1 percent by weight of the polymer.

Examples of specific polymers useful in the present invention are included in Table 1 which are also discussed in the examples where all weights used in the polymerization are shown in grams with the percentage of the monomers in the polymer shown in parenthesis based on the total of all monomers and crosslinking agents and assuming incorporation of all monomers and crosslinkers in the polymers.

TABLE 1

| Examples | EOEMA (g (%)) | HEMA (g (%)) | EGDMA (g) | TMPTMA (g) | Initiator g | Water Content (%) |
|---|---|---|---|---|---|---|
| 1 | 92 (91.45) | 8 (7.95) | 0.1 | 0.5 | 0.07 | 3.6 |
| 2 | 90 (89.46) | 10 (9.94) | 0.1 | 0.5 | 0.07 | 4.0 |
| 3 | 88 (87.48) | 12 (11.93) | 0.1 | 0.5 | 0.07 | 4.2 |
| 4 | 96 (95.43) | 4 (3.98) | 0.1 | 0.5 | 0.07 | 2.4 |
| 5 | 92 (91.45) | 8 (7.95) | 0.1 | 0.5 | 0.07 | 3.1 |
| 6 | 88 (87.48) | 12 (11.93) | 0.1 | 0.5 | 0.07 | 4.0 |
| 7 | 98 (96.84) | 2 (1.98) | 0.2 | 1.0 | 0.07 | 2.3 |
| 8 | 96 (94.86) | 4 (3.95) | 0.2 | 1.0 | 0.07 | 2.4 |
| 9 | 92 (90.91) | 8 (7.91) | 0.2 | 1.0 | 0.07 | 3.3 |
| p-HEMA/ EOEMA | 25 | 75 | 0.13 max | 0.5 | | 25.0 |
| p-HEMA | 0 | 99 | | | | 38.0 |
| p-EOEMA | 99 | 0 | | | | 1.5 |

These polymers are formed using the same procedures disclosed in Example 1. 2,2-Azobis(2,4-dimethylvaleronitrile) was used as an initiator to prepare the polymers of each of Examples 1-9 in an amount of about 0.07 weight percent based on the total weight of the monomers.

Unfolding was measured at 36° C. for the examples in Table 1. Examples 1-9 each unfolded at times of less than 150 seconds. The CT (central thickness) for lenses formed from the polymers of Examples 1-9 ranged from 0.9 mm to 1.2 mm. The thickness of haptics formed from the polymer of each of Examples 1-9 ranged from 0.5 mm to 0.8 mm. The refractive index at 22° C. for the polymers of Examples 1-9 were 1.48.

Lenses formed from the polymers described in Table 1 do not develop readily observable bubbles or voids in the matrix when such lenses are placed in a saline solution at 40° C. overnight and allowed to cool room temperature. Therefore, no glistening is observed for these lenses. Therefore, in some embodiments, lenses formed from the polymers of the invention do not form bubbles when placed in a saline solution at 40° C. overnight and then cooled to room temperature.

Lenses formed from the polymers described in Table 1 also have very favorable unfolding properties. For example, lenses formed from the polymers of Table 1 unfold in less than or about 2 minutes when placed in a saline solution at 37° C. The average thickness of these lenses is generally less than 1 mm such as lenses with a central thickness of from 0.793 mm to 0.999 mm. In some embodiments, the lenses unfold in times of less than 1 minute and in still other embodiments, they unfold in less than or about 30 seconds.

The polymers used in the intraocular lenses preferably have a refractive index (RI) of greater than or about 1.4 generally from about 1.4 to about 1.5. An advantage of polymers of the present invention is that they can be folded prior to insertion, thereby reducing the size of the incision. The RI value of a material influences the design and the parameters of an intraocular lens. Hence, besides biocompatibility, an ideal intraocular lens is foldable and injectable, and has the ability to quickly regain its shape and optical quality after insertion, and has a high RI value. The intraocular lenses of the present invention have been found to possess these desired characteristics. Furthermore, the hydrophobic nature of lenses formed from the polymers of the invention provides lenses that are more resistant to opacification. Thus, the intraocular lenses of the present invention fulfill the requirements of a high performance intraocular lens and have excellent folding characteristics, a relatively high refraction index, excellent unfolding characteristics, and have improved opacification-resistance properties.

Initial results show that as the hydrophilic content increases, so does the stiffness ($T_g$) of the polymer. When cut into discs and hydrated, the materials show a wide range of flexibility that appears to vary inversely with the water content, at least within range of compositions shown in Table 1. Initial studies indicate that the polymer compositions of the invention possess useful and favorable thermal and mechanical properties.

The intraocular lenses of the present invention may be formed by methods known in the art. For example, in an exemplary process the monomers that form the polymer are polymerized into a polymer rod, polymer blanks or discs are formed from the rod, and then the blanks are cut, for example, by a lathe into the intraocular lens. The rods can be made by a procedure which begins with polymerizing, in a mold, such as in a tubular or cylindrical mold, a mixture of initiator and monomers, to form an optically clear soft lens body. As discussed above, it may be desirable to incorporate cross-linking materials and ultraviolet-absorbing compounds during polymerization or into the resultant polymer matrix. In some embodiments the polymer rods are then cut and ground or otherwise machined, into blanks of the desired diameter and thickness by lathe cutting and machine milled at temperatures below the $T_g$ into an intraocular lens.

Generally, the composite material rod is lathe cut or ground to a diameter 0.5 to 2.0 mm thicker than the required distance from the center of the lens body to the furthest edge of the legs or haptics. This rod is then cut into blanks of uniform thickness. The blanks are ground and lapped to a diameter and thickness suitable for lathe cutting and machine milling in the conventional manner into the intraocular lens of the present invention. Because the present polymers may have low glass transition temperatures, the rod or blanks may require cooling below $T_g$ prior to and/or during cutting, lathing and/or milling.

A general description of a stepwise process for forming the blanks into intraocular lenses is set forth in the flow chart below. One having ordinary skill in the field of intraocular lens manufacturing, from a review of the present specification, can make intraocular lenses using the general knowledge in the art on intraocular lens manufacture and the process of cryogenic machining.

Intraocular lenses can also be made by molding the present polymer to form all or part of the optic portion of the lens. For example, the present polymer can be polymerized in a mold by a liquid mixture of monomers and additional components, to form an optically clear soft lens body. These molding methods can involve molding the optics on one half of the lens, such as the anterior or posterior portion, or fully molding the lens. When only half of the optic portion of the lens is formed in the mold then the second side optics can be machined, for example as discussed above. In either of these embodiments, additional material can be molded to allow machining of various haptic designs.

The invention is illustrated by the following non-limiting examples.

EXAMPLES

EOEMA refers to ethoxyethyl methacrylate
HEMA refers to 2-hydroxyethyl methacrylate
TMPTMA refers to trimethylol propane trimethacrylate
EGDMA refers to ethylene glycol dimethacrylate

Example 1

Ethoxyethyl methacrylate (EOEMA) (92 g) was mixed with 8 grams of 2-hydroxyethyl methacrylate (HEMA), 0.5 grams of trimethylol propane trimethacrylate (TMPTMA) and 0.1 grams of ethylene glycol dimethacrylate (EGDMA) without solvent. The mixture was degassed while applying vigorous stirring. The mixture was dispensed into cylindrical molds, polymerized at 30° C. for 15 to 30 hours, and post-cured at up to 100° C. for 5 hours. The polymer was then removed from the molds, the cylindrical molds were ground to 0.5 to 0.65 inches (1.27 to 1.65 cm.) in diameter, and formed into blanks. The mechanical formation process comprised cutting the polymer into cylinders of 0.1 to 0.2 inches (0.25 to 0.51 cm.) in thickness.

Procedures for Machining Polymers

Sample optics may be cut using a DAC lathe with a freezing or cooling device attached to the collet of a DAC-Vision lathe. The freezing apparatus allowed polymer blanks to be affixed to a steel mandrel using moisture/ice. Freezing served two purposes: 1) it cooled the acrylic rubber to below its $T_g$ allowing for ease of cutting of the surface and 2) it allowed the icy surface to fix the blank in position for cutting. All materials will exhibit an optimal temperature for this operation which may vary as known by those skilled in the art, but will always be below the $T_g$ of the polymer. For examples 7 through 10, the following conditions were used. The rough and fine tools consisted of single point diamond tools 0.5 mm and 0.3 mm in radius, respectively. The blank surface temperature on the cooling device ranged from 5° C. to −5° C., and the DAC lathe run parameters used are listed in the following table:

|  | Rough Tool | Fine Tool |
| --- | --- | --- |
| Spindle Speed | 10,000 rpm | 9,500 rpm |
| Feed Rate | 0.66 in/min | 0.33 in/min |
| Depth of Cut | 0.2 mm | 0.07 mm |

The present compositions can have any or all of the components described herein. Likewise, the present methods can be carried out by performing any of the steps described herein, either alone or in various combinations. One skilled in the art will recognize that all embodiments of the present invention are capable of use with all other appropriate embodiments of the invention described herein. Additionally, one skilled in the art will realize that the present invention also encompasses variations of the present probes, configurations and methods that specifically exclude one or more of the components or steps described herein.

The following is a list of non-limiting embodiments of optic portions of an intraocular lens, in accordance with the present invention.

An optic portion of an intraocular lens, the optic portion comprising a polymer that comprises, consists of, or consists essentially of:
(a) one or more alkoxyalkyl methacrylate monomers and/or one or more alkoxyalkyl acrylate monomers that are incorporated in the polymer;
(b) one or more hydroxyalkyl methacrylate monomers and/or one or more hydroxyalkyl acrylate monomers that are incorporated in the polymer; and
(c) optionally, one or more crosslinking agents that are incorporated in the polymer,
wherein the total combined weight of the one or more alkoxyalkyl methacrylate monomers and the one or more alkoxyalkyl acrylate monomers ranges from 75 percent to 99 percent based on the total weight of the dry polymer, and the total combined weight of the one or more hydroxyalkyl methacrylate monomers and the one or more hydroxyalkyl acrylate monomers ranges from 1 percent to 25 percent based on the total weight of the dry polymer.

An intraocular lens, wherein the intraocular lens comprises one or more haptic portion and the optic portion of the preceding paragraph.

The intraocular lens of the preceding paragraph, wherein the optic portion and the one or more haptic portion are made of the same polymer. The intraocular lens of the preceding paragraph, wherein the optic portion and the one or more haptic portion are part of a one piece intraocular lens. The intraocular lens of preceding paragraph, wherein the optic portion and the one or more haptic portions are made of different materials. The intraocular lens of preceding paragraph, wherein the optic portion and the one or more haptic portions form a multiple piece intraocular lens. The intraocular lens of preceding paragraph, further comprising a polymer surrounding the optic portion, wherein the polymer surrounding the optic portion is not the same as the polymer of the optic portion.

The optic portion or the intraocular lens of any embodiment described in the two preceding paragraphs, wherein the one or more alkoxyalkyl methacrylate monomers have the formula $R_1$—O—$R_2$-MA prior to being incorporated in the polymer, and the one or more alkoxyalkyl acrylate monomers have the formula, $R_3$—O—$R_4$-A prior to being incorporated in the polymer, wherein MA is methacrylate, A is acrylate, and $R_1$, $R_2$, $R_3$, and $R_4$ are independently selected from alkyl groups having from 1 to 5 carbon atoms.

The optic portion or the intraocular lens of the preceding paragraph, wherein $R_1$ and $R_3$ have from 1 to 3 carbon atoms, and $R_2$ and $R_4$ have 2 or 3 carbon atoms. The optic portion or the intraocular lens of the preceding paragraph, wherein $R_1$ and $R_3$ have 2 carbon atoms, and $R_2$ and $R_4$ have 2 carbon atoms. The optic portion or the intraocular lens of the preceding paragraph, wherein the polymer of the optic portion comprises incorporated ethoxyethyl methacrylate. Regarding the immediately preceding embodiment, the total weight of the ethoxyethyl methacrylate may range from 80 percent to 98 percent based on the total weight of the dry polymer of the optic portion, or from 86 percent to 98 percent based on the total weight of the dry polymer of the optic portion.

The optic portion or the intraocular lens of any one of the preceding, non-limiting embodiments, wherein the one or more hydroxyalkyl methacrylate monomers have the formula HO—$R_5$-MA prior to being incorporated in the polymer, and the one or more hydroxyalkyl acrylate monomers have the formula, HO—$R_6$-A prior to being incorporated in the polymer, wherein MA is methacrylate, A is acrylate, and $R_5$ and $R_6$ are independently selected from alkyl groups having from 1 to 4 carbon atoms.

The optic portion or the intraocular lens of the preceding paragraph, wherein $R_5$ and $R_6$ have from 2 to 3 carbon atoms. The optic portion or the intraocular lens of the preceding paragraph, wherein $R_5$ and $R_6$ have 2 carbon atoms. The optic portion or the intraocular lens of the preceding paragraph, wherein the polymer of the optic portion comprises incorporated 2-hydroxyethyl methacrylate. Regarding the immediately preceding embodiment, the total weight of the 2-hydroxyethyl methacrylate may range from 1 percent to 20 percent based on the total weight of the dry polymer of the optic portion, or from 1 percent to 12 percent based on the total weight of the dry polymer of the optic portion.

The optic portion or the intraocular lens of any one of the preceding non-limiting embodiments, wherein the polymer of the optic portion comprises, the one or more crosslinking agents that are incorporated in the polymer.

The optic portion or the intraocular lens of the preceding paragraph, wherein at least one of the one or more crosslinking agents is a di-functional crosslinking agent prior to incorporation in the polymer, and particularly, wherein the di-functional crosslinking agent is selected from ethylene glycol dimethacrylate prior to being incorporated in the polymer or tetraethylene glycol dimethacrylate prior to being incorporated in the polymer.

The optic portion or the intraocular lens of the preceding paragraph, wherein the polymer of the optic portion comprises incorporated ethylene glycol dimethacrylate, and the total weight of the ethylene glycol dimethacrylate ranges from 0.05 percent to 0.5 percent based on the total weight of the dry polymer of the optic portion, or from 0.08 percent to 0.25 percent based on the total weight of the dry polymer of the optic portion.

The optic portion or the intraocular lens of any one of the preceding three paragraphs, wherein at least one of the one or more crosslinking agents is a multi-functional crosslinking agent prior to incorporation in the polymer.

The optic portion or the intraocular lens of the preceding paragraph, wherein the multi-functional crosslinking agent is selected from trimethylol propane trimethacrylate or trimethylol propane triacrylate prior to being incorporated in the polymer.

The optic portion or the intraocular lens of the preceding paragraph, wherein the polymer of the optic portion comprises incorporated trimethylol propane trimethacrylate and/or trimethylol propane triacrylate, and the total combined weight of the trimethylol propane trimethacrylate and the trimethylol propane triacrylate ranges from 0.3 percent to 1.5 percent based on the total weight of the dry polymer of the optic portion, or from 0.45 percent to 1.2 percent based on the total weight of the dry polymer of the optic portion, or from 0.5 percent to 1.0 percent based on the total weight of the dry polymer of the optic portion.

The optic portion or the intraocular lens of any one of the preceding non-limiting embodiments, wherein the polymer of the optic portion further comprises water.

The optic portion or the intraocular lens of any one of the preceding, non-limiting embodiments, wherein the polymer of the optic portion further comprises one or more ultraviolet absorbing compounds and/or one or more ultraviolet absorbing monomer that is incorporated in the polymer of optic portion.

An optic portion or an intraocular lens comprising a polymer that comprises, consists of, or consists essentially of:

(a) an incorporated alkoxyalkyl methacrylate in an amount of from 87 percent to 98 percent by weight based on the total weight of the dry polymer;
(b) an incorporated hydroxyalkyl methacrylate in an amount of from 1.5 percent to 12 percent by weight based on the total weight of the dry polymer;
(c) an incorporated di-functional methacrylate and/or di-functional acrylate crosslinking agent in an amount ranging from 0.085 percent to 0.2 percent based on the total weight of the dry polymer;
(d) an incorporated multi-functional methacrylate and/or multifunctional acrylate crosslinking agent in an amount ranging from 0.4 percent to 1 percent based on the total weight of the dry polymer; and
(e) optionally one or more additional ingredients selected from water, a ultraviolet absorbing compound or monomer, a colorant, or an antioxidant.

The optic portion or the intraocular lens of the preceding paragraph, wherein the alkoxyalkyl methacrylate is ethoxyethyl methacrylate, the hydroxyalkyl methacrylate is 2-hydroxyethyl methacrylate, the di-functional methacrylate and/or acrylate crosslinking agent is ethylene glycol dimethacrylate, and the multi-functional methacrylate and/or acrylate crosslinking agent is trimethylol propane trimethacrylate.

The optic portion or the intraocular lens of any preceding non-limiting embodiment, wherein the glass transition temperature of the polymer of the optic portion is below about 35° C.

The optic portion or the intraocular lens of the preceding paragraph, wherein the glass transition temperature of the polymer of the optic portion is from about −25° C. to about 35° C., or from about −5° C. to about 15° C.

The optic portion or the intraocular lens of any preceding, non-limiting embodiment, wherein the polymer of the optic portion has a refractive index of 1.40 or higher, or of 1.46 or higher, or of 1.48 or higher.

The optic portion or the intraocular lens of any preceding, non-limiting embodiment, wherein the polymer of the optic portion comprises water, and the equilibrium water content is less than or about 5 percent based on the weight of the polymer after it is hydrated.

The optic portion or the intraocular lens of the preceding paragraph, wherein the equilibrium water content ranges from 2 percent to 4.5 percent based on the weight of the polymer after it is hydrated, or from 2.3 percent to 4.2 percent based on the weight of the polymer after it is hydrated.

The optic portion or the intraocular lens of any preceding, non-limiting embodiment wherein the polymer of the optic portion contains substantially no aromatic polymer.

The following is a list of non-limiting embodiments of polymers, in accordance with the present invention.

A polymer that comprises, consists of, or consists essentially of:
(a) one or more alkoxyalkyl methacrylate monomers and/or one or more alkoxyalkyl acrylate monomers that are incorporated in the polymer;
(b) one or more hydroxyalkyl methacrylate monomers and/or one or more hydroxyalkyl acrylate monomers that are incorporated in the polymer; and
(c) optionally, one or more crosslinking agents that are incorporated in the polymer,
wherein the total combined weight of the one or more alkoxyalkyl methacrylate monomers and the one or more alkoxyalkyl acrylate monomers ranges from 75 percent to 99 percent based on the total weight of the dry polymer, and the total combined weight of the one or more hydroxyalkyl methacrylate monomers and the one or more hydroxyalkyl acrylate monomers ranges from 1 percent to 25 percent based on the total weight of the dry polymer.

The polymer of the preceding paragraph, wherein the one or more alkoxyalkyl methacrylate monomers have the formula $R_1$—O—$R_2$-MA prior to being incorporated in the polymer, and the one or more alkoxyalkyl acrylate monomers have the formula, $R_3$—O—$R_4$-A prior to being incorporated in the polymer, wherein MA is methacrylate, A is acrylate, and $R_1$, $R_2$, $R_3$, and $R_4$ are independently selected from alkyl groups having from 1 to 5 carbon atoms.

The polymer of the preceding paragraph, wherein $R_1$ and $R_3$ have from 1 to 3 carbon atoms, and $R_2$ and $R_4$ have 2 or 3 carbon atoms. The polymer of the preceding paragraph, wherein $R_1$ and $R_3$ have 2 carbon atoms, and $R_2$ and $R_4$ have 2 carbon atoms. The polymer of the preceding paragraph, wherein the polymer comprises incorporated ethoxyethyl methacrylate, and particularly wherein the total weight of the ethoxyethyl methacrylate ranges from 80 percent to 98 percent based on the total weight of the dry polymer, or from 86 percent to 98 percent based on the total weight of the dry polymer.

The polymer of any preceding, non-limiting embodiment, wherein the one or more hydroxyalkyl methacrylate monomers have the formula HO—$R_5$-MA prior to being incorporated in the polymer, and the one or more hydroxyalkyl acrylate monomers have the formula, HO—$R_6$-A prior to being incorporated in the polymer, wherein MA is methacrylate, A is acrylate, and $R_5$ and $R_6$ are independently selected from alkyl groups having from 1 to 4 carbon atoms.

The polymer of the preceding paragraph, wherein $R_5$ and $R_6$ have from 2 to 3 carbon atoms. The polymer of the preceding paragraph, wherein $R_5$ and $R_6$ have 2 carbon atoms. The polymer of the preceding paragraph, wherein the polymer comprises incorporated 2-hydroxyethyl methacrylate, and particularly wherein the total weight of the 2-hydroxyethyl methacrylate ranges from 1 percent to 20 percent based on the total weight of the dry polymer, or from 1 percent to 12 percent based on the total weight of the dry polymer.

The polymer of any preceding, non-limiting embodiment, wherein the polymer comprises, the one or more crosslinking agents that are incorporated in the polymer.

The polymer of the preceding paragraph, wherein the one or more crosslinking agents include a di-functional crosslinking agent is selected from ethylene glycol dimethacrylate prior to being incorporated in the polymer or tetraethylene glycol dimethacrylate prior to being incorporated in the polymer.

The polymer of the preceding paragraph, wherein the polymer comprises incorporated ethylene glycol dimethacrylate, and the total weight of the ethylene glycol dimethacrylate ranges from 0.05 percent to 0.5 percent based on the total weight of the dry polymer, or from 0.08 percent to 0.25 percent based on the total weight of the dry polymer, or from 0.1 percent to 0.2 percent based on the total weight of the dry polymer.

The polymer of any one of the three preceding paragraphs, wherein at least one of the one or more crosslinking agents is a multi-functional crosslinking agent prior to incorporation in the polymer.

The polymer of the preceding paragraph, wherein the multi-functional crosslinking agent is selected from trimethylol propane trimethacrylate or trimethylol propane triacrylate prior to being incorporated in the polymer.

The polymer of the preceding paragraph, wherein the polymer comprises incorporated trimethylol propane trimethacrylate and/or trimethylol propane triacrylate, and the total combined weight of the trimethylol propane trimethacrylate and the trimethylol propane triacrylate ranges from 0.3 percent to 1.5 percent based on the total weight of the dry polymer, or from 0.45 percent to 1.2 percent based on the total weight of the dry polymer, or from 0.5 percent to 1.0 percent based on the total weight of the dry polymer.

The polymer of any preceding, non-limiting embodiment, wherein the polymer further comprises water.

The polymer of any preceding, non-limiting embodiment, wherein the polymer of the further comprises one or more ultraviolet absorbing compounds and/or one or more ultraviolet absorbing monomer that is incorporated in the polymer of optic portion.

A polymer that comprises, consists of, or consists essentially of:
(a) an incorporated alkoxyalkyl methacrylate in an amount of from 87 percent to 98 percent by weight based on the total weight of the dry polymer;
(b) an incorporated hydroxyalkyl methacrylate in an amount of from 1.5 percent to 12 percent by weight based on the total weight of the dry polymer;
(c) an incorporated di-functional methacrylate and/or di-functional acrylate crosslinking agent in an amount ranging from 0.085 percent to 0.2 percent based on the total weight of the dry polymer;
(d) an incorporated multi-functional methacrylate and/or multifunctional acrylate crosslinking agent in an amount ranging from 0.4 percent to 1 percent based on the total weight of the dry polymer; and
(e) optionally one or more additional ingredients selected from water, a ultraviolet absorbing compound or monomer, a colorant, or an antioxidant.

The polymer of the preceding paragraph, wherein the alkoxyalkyl methacrylate is ethoxyethyl methacrylate, the hydroxyalkyl methacrylate is 2-hydroxyethyl methacrylate, the di-functional methacrylate and/or acrylate crosslinking agent is ethylene glycol dimethacrylate, and the multi-functional methacrylate and/or acrylate crosslinking agent is trimethylol propane trimethacrylate.

The polymer of any preceding non-limiting embodiment, wherein the polymer comprises water, and the equilibrium water content is less than or about 5 percent based on the weight of the polymer after it is hydrated, or from 2 percent to 4.5 percent based on the weight of the polymer after it is hydrated, or from 2.3 percent to 4.2 percent based on the weight of the polymer after it is hydrated.

The polymer of any one of the preceding, non-limiting embodiments, wherein the polymer contains substantially no aromatic polymer.

The following is a list of non-limiting embodiments of methods for manufacturing a polymer, in accordance with the present invention.

A method for manufacturing a polymer, comprising:
(a) polymerizing a mixture to form the polymer, wherein the mixture comprises, consists of, or consists essentially of:
  (i) one or more alkoxyalkyl methacrylate monomers and/or one or more alkoxyalkyl acrylate monomers;
  (ii) one or more hydroxyalkyl methacrylate monomers and/or one or more hydroxyalkyl acrylate monomers;
  (iii) optionally, one or more crosslinking agents; and
  (iv) optionally, one or more initiator,
wherein the total combined weight of the one or more alkoxyalkyl methacrylate monomers and the one or more alkoxyalkyl acrylate monomers in the mixture ranges from 75 percent to 99 percent based on the total combined weight of the one or more alkoxyalkyl methacrylate monomers, the one or more alkoxyalkyl acrylate monomers, the one or more hydroxyalkyl methacrylate monomers, the one or more hydroxyalkyl acrylate monomers, and the one or more crosslinking agents in the mixture, and the total combined weight of the one or more hydroxyalkyl methacrylate monomers and the one or more hydroxyalkyl acrylate monomers in the mixture ranges from 1 percent to 25 percent based on the total combined weight of the one or more alkoxyalkyl methacrylate monomers, the one or more alkoxyalkyl acrylate monomers, the one or more hydroxyalkyl methacrylate monomers, the one or more hydroxyalkyl acrylate monomers, and the one or more crosslinking agents in the mixture.

The method for manufacturing the polymer of the preceding paragraph, wherein the mixture is polymerized in a mold and, optionally, further comprising forming an intraocular lens from the polymer. The method for manufacturing the polymer of the preceding paragraph, further comprising forming an optic portion of an intraocular lens from the polymer, and optionally, further comprising forming an intraocular lens from the optic portion.

The method for manufacturing the polymer of any one of the preceding, non-limiting embodiments, wherein the one or more alkoxyalkyl methacrylate monomers have the formula $R_1$—O—$R_2$-MA, and the one or more alkoxyalkyl acrylate monomers have the formula, $R_3$—O—$R_4$-A, wherein MA is methacrylate, A is acrylate, and $R_1$, $R_2$, $R_3$, and $R_4$ are independently selected from alkyl groups having from 1 to 5 carbon atoms.

The method for manufacturing the polymer of the preceding paragraph, wherein $R_1$ and $R_3$ have from 1 to 3 carbon atoms, and $R_2$ and $R_4$ have 2 or 3 carbon atoms. The method for manufacturing the polymer of the preceding paragraph, wherein $R_1$ and $R_3$ have 2 carbon atoms, and $R_2$ and $R_4$ have 2 carbon atoms. The method for manufacturing the polymer of the preceding paragraph, wherein the mixture comprises ethoxyethyl methacrylate, and particularly wherein the total weight of the ethoxyethyl methacrylate in the mixture ranges from 80 percent to 98 percent (or from 86 percent to 98 percent) based on the total combined weight of the one or more alkoxyalkyl methacrylate monomers, the one or more alkoxyalkyl acrylate monomers, the one or more hydroxyalkyl methacrylate monomers, the one or more hydroxyalkyl acrylate monomers, and the one or more crosslinking agents in the mixture, or The method for manufacturing the polymer of any preceding, non-limiting embodiment, wherein the one or more hydroxyalkyl methacrylate monomers have the formula HO—$R_5$-MA, and the one or more hydroxyalkyl acrylate monomers have the formula, HO—$R_6$-A, wherein MA is methacrylate, A is acrylate, and $R_5$ and $R_6$ are independently selected from alkyl groups having from 1 to 4 carbon atoms.

The method for manufacturing the polymer of the preceding paragraph, wherein $R_5$ and $R_6$ have from 2 to 3 carbon atoms. The method for manufacturing the polymer of the preceding paragraph, wherein $R_5$ and $R_6$ have 2 carbon atoms. The method for manufacturing the polymer of the preceding paragraph, wherein the mixture comprises 2-hydroxyethyl methacrylate, particularly wherein the total weight of the 2-hydroxyethyl methacrylate in the mixture ranges from 1 percent to 12 percent based on the total combined weight of the one or more alkoxyalkyl methacrylate monomers, the one or more alkoxyalkyl acrylate monomers, the one or more hydroxyalkyl methacrylate monomers, the one or more hydroxyalkyl acrylate monomers, and the one or more crosslinking agents in the mixture.

The method for manufacturing the polymer of any preceding, non-limiting embodiment, wherein the mixture comprises, the one or more crosslinking agents.

The method for manufacturing the polymer of the preceding paragraph, wherein at least one of the one or more crosslinking agents is a di-functional crosslinking agent.

The method for manufacturing the polymer of the preceding paragraph, wherein the di-functional crosslinking agent is selected from ethylene glycol dimethacrylate or tetraethylene glycol dimethacrylate.

The method for manufacturing the polymer of the preceding paragraph, wherein the di-functional crosslinking agent comprises ethylene glycol dimethacrylate, and the total weight of the ethylene glycol dimethacrylate in the mixture ranges from 0.05 percent to 0.5 percent (or from 0.08 percent to 0.25 percent, or from 0.1 percent to 0.2 percent) based on the total combined weight of the one or more alkoxyalkyl methacrylate monomers, the one or more alkoxyalkyl acrylate monomers, the one or more hydroxyalkyl methacrylate monomers, the one or more hydroxyalkyl acrylate monomers, and the one or more crosslinking agents in the mixture.

The method for manufacturing the polymer of any preceding, non-limiting embodiment, wherein at least one of the one or more crosslinking agents is a multi-functional crosslinking agent.

The method for manufacturing the polymer of the preceding paragraph, wherein the multi-functional crosslinking agent is selected from trimethylol propane trimethacrylate or trimethylol propane triacrylate.

The method for manufacturing the polymer of the preceding paragraph, wherein the crosslinking agent comprises trimethylol propane trimethacrylate and/or trimethylol propane triacrylate, and the total combined weight of the trimethylol propane trimethacrylate and the trimethylol propane triacrylate in the mixture ranges from 0.3 percent to 1.5 percent (or from 0.45 percent to 1.2 percent or from 0.5 percent to 1.0 percent) based on the total combined weight of the one or more alkoxyalkyl methacrylate monomers, the one or more alkoxyalkyl acrylate monomers, the one or more hydroxyalkyl methacrylate monomers, the one or more hydroxyalkyl acrylate monomers, and the one or more crosslinking agents in the mixture.

The method for manufacturing the polymer of any preceding, non-limiting embodiment, wherein the mixture further comprises one or more ultraviolet absorbing compounds and/or one or more ultraviolet absorbing monomer.

The method for manufacturing the polymer from a mixture that comprises, consists of, or consists essentially of:

(a) an alkoxyalkyl methacrylate, wherein the alkoxyalkyl methacrylate is present in the mixture in an amount of from 87 percent to 98 percent by weight based on the total combined weight of the one or more alkoxyalkyl methacrylate monomers, the one or more alkoxyalkyl acrylate monomers, the one or more hydroxyalkyl methacrylate monomers, the one or more hydroxyalkyl acrylate monomers, and the one or more crosslinking agents in the mixture;

(b) a hydroxyalkyl methacrylate, wherein the hydroxyalkyl methacrylate is present in the mixture in an amount of from 1.5 percent to 12 percent by weight based on the total combined weight of the one or more alkoxyalkyl methacrylate monomers, the one or more alkoxyalkyl acrylate monomers, the one or more hydroxyalkyl methacrylate monomers, the one or more hydroxyalkyl acrylate monomers, and the one or more crosslinking agents in the mixture;

(c) a di-functional methacrylate and/or di-functional acrylate crosslinking agent, wherein the combined weight of the di-functional methacrylate and/or the di-functional acrylate crosslinking agent in the mixture ranges from 0.085 percent to 0.2 percent based on the total combined weight of the one or more alkoxyalkyl methacrylate monomers, the one or more alkoxyalkyl acrylate monomers, the one or more hydroxyalkyl methacrylate monomers, the one or more hydroxyalkyl acrylate monomers, and the one or more crosslinking agents in the mixture;

(d) a multi-functional methacrylate and/or multifunctional acrylate crosslinking agent, wherein the combined weight of the multi-functional methacrylate and/or the multi-functional acrylate crosslinking agent in the mixture ranges from 0.4 percent to 1 percent based on the total combined weight of the one or more alkoxyalkyl methacrylate monomers, the one or more alkoxyalkyl acrylate monomers, the one or more hydroxyalkyl methacrylate monomers, the one or more hydroxyalkyl acrylate monomers, and the one or more crosslinking agents in the mixture; and (e) optionally one or more additional ingredients selected from an initiator, an ultraviolet absorbing compound or monomer, a colorant, or an antioxidant.

The method for manufacturing the polymer of the preceding paragraph, wherein the alkoxyalkyl methacrylate is ethoxyethyl methacrylate, the hydroxyalkyl methacrylate is 2-hydroxyethyl methacrylate, the di-functional methacrylate and/or acrylate crosslinking agent is ethylene glycol dimethacrylate, and the multi-functional methacrylate and/or acrylate crosslinking agent is trimethylol propane trimethacrylate.

The method for manufacturing the polymer of any one of the preceding non-limiting embodiments, wherein the equilibrium water content is less than or about 5 percent based on the weight of the polymer after it is hydrated.

The method for manufacturing the polymer of the preceding paragraph, wherein the equilibrium water content ranges from 2 percent to 4.5 percent based on the weight of the polymer after it is hydrated. The method for manufacturing the polymer of the preceding paragraph, wherein the equilibrium water content ranges from 2.3 percent to 4.2 percent based on the weight of the polymer after it is hydrated.

The method for manufacturing the polymer of any preceding, non-limiting embodiment, wherein the mixture contains substantially no aromatic polymer. The method of any preceding, non-limiting embodiment, wherein the mixture comprises less than 2 percent by weight of any aromatic component.

A method for modifying an individual's eyesight, comprising inserting the intraocular lens or the intraocular lens made from the optic portion of any preceding, non-limiting embodiment into an eye of a subject.

The method for modifying an individual's eyesight of the preceding paragraph, further comprising folding the intraocular lens prior to inserting the intraocular lens into the eye and allowing the intraocular lens to unfold after it is inserted into the eye of the subject.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," "more than" and the like include the number recited and refer to ranges which can be subsequently broken down into subranges as discussed above. In the same manner, all ratios disclosed herein also include all subratios falling within the broader ratio.

One skilled in the art will also readily recognize that where members are grouped together in a common manner, such as in a Markush group, the present invention encompasses not only the entire group listed as a whole, but each member of the group individually and all possible subgroups of the main group. Accordingly, for all purposes, the present invention encompasses not only the main group, but also the main group absent one or more of the group members. The present invention also envisages the explicit exclusion of one or more of any of the group members in the claimed invention.

All references, patents, and publications disclosed herein are specifically incorporated by reference in their entireties and for all purposes as if fully set forth in their entireties. Unless otherwise specified, "a" or "an" means "one or more".

While preferred embodiments have been illustrated and described, it should be understood that changes and modifications can be made therein in accordance with ordinary skill in the art without departing from the invention in its broader aspects as defined in the following claims.

What is claimed is:

1. A polymer that comprises:
    (a) ethoxyethyl methacrylate monomers and/or ethoxyethyl acrylate monomers that are incorporated in the polymer;
    (b) one or more hydroxyalkyl methacrylate monomers and/or one or more hydroxyalkyl acrylate monomers that are incorporated in the polymer; and
    (c) one or more di-functional crosslinking agents that are incorporated in the polymer, and
    (d) one or more multifunctional crosslinking agents, different from the one or more di-functional crosslinking agents, that are incorporated in the polymer,
    wherein the total combined weight of the ethoxyethyl methacrylate monomers and the ethoxyethyl acrylate monomers ranges from 87 percent to 98 percent based on the total weight of the dry polymer, and the total combined weight of the one or more hydroxyalkyl methacrylate monomers and the one or more hydroxyalkyl acrylate monomers ranges from 1.5 percent to 12 percent based on the total weight of the dry polymer, and wherein 5 percent or less based on the total weight of the dry polymer of the monomers incorporated in the polymer have aromatic constituents, and wherein the polymer is prepared by polymerization without solvent.

2. The polymer of claim 1, wherein the polymer comprises incorporated ethoxyethyl methacrylate.

3. The polymer of claim 2, wherein the polymer comprises incorporated ethoxyethyl methacrylate, and the total weight of the ethoxyethyl methacrylate ranges from 88 percent to 98 percent based on the total weight of the dry polymer.

4. The polymer of claim 1, wherein the one or more hydroxyalkyl methacrylate monomers have the formula HO—$R_5$-MA prior to being incorporated in the polymer, and the one or more hydroxyalkyl acrylate monomers have the formula, HO—$R_6$-A prior to being incorporated in the polymer, wherein MA is methacrylate, A is acrylate, and $R_5$ and $R_6$ are independently selected from alkyl groups having from 1 to 4 carbon atoms.

5. The polymer of claim 4, wherein the polymer comprises incorporated 2-hydroxyethyl methacrylate.

6. The polymer of claim 5, wherein the polymer comprises incorporated 2-hydroxyethyl methacrylate, and the total weight of the 2-hydroxyethyl methacrylate ranges from 2 percent to 10 percent based on the total weight of the dry polymer.

7. The polymer of claim 1, wherein the one or more di-functional crosslinking agents that are incorporated in the polymer are selected from ethylene glycol dimethacrylate prior to being incorporated in the polymer, and tetraethylene glycol dimethacrylate prior to being incorporated in the polymer.

8. The polymer of claim 1, wherein the one or more multifunctional crosslinking agents are selected from trimethylol propane trimethacrylate prior to being incorporated in the polymer, and trimethylol propane tricrylate prior to being incorporated into the polymer.

9. The polymer of claim 1, wherein the polymer further comprises one or more ultraviolet absorbing compounds and/or one or more ultraviolet absorbing monomer that is incorporated in the polymer.

10. The polymer of claim 1, wherein the polymer comprises:
    (a) an incorporated ethoxyethyl methacrylate in an amount of from 90 percent to 98 percent by weight based on the total weight of the dry polymer;
    (b) an incorporated hydroxyalkyl methacrylate in an amount of from 1.5 percent to 10 percent by weight based on the total weight of the dry polymer;
    (c) an incorporated di-functional methacrylate and/or di-functional acrylate crosslinking agent in an amount ranging from 0.085 percent to 0.2 percent based on the total weight of the dry polymer;
    (d) an incorporated multi-functional methacrylate and/or multifunctional acrylate crosslinking agent different from the incorporated di-functional methacrylate and/or di-functional acrylate crosslinking agent, in an amount ranging from 0.4 percent to 1 percent based on the total weight of the dry polymer; and
    (e) optionally one or more additional ingredients selected from water, an ultraviolet absorbing compound or monomer, a colorant, or an antioxidant.

11. The polymer of claim 10, wherein the hydroxyalkyl methacrylate is 2-hydroxyethyl methacrylate, the di-functional methacrylate and/or acrylate crosslinking agent is ethylene glycol dimethacrylate, and the multi-functional methacrylate and/or acrylate crosslinking agent is trimethylol propane trimethacrylate.

12. The polymer of claim 1, wherein the polymer comprises water, and the equilibrium water content is less than or about 5 percent based on the weight of the polymer after it is hydrated.

13. The polymer of claim 1, wherein the polymer contains substantially no aromatic polymer.

14. The polymer of claim 9, wherein the polymer comprises one or more ultraviolet absorbing monomer that is incorporated in the polymer.

15. The polymer of claim 14, wherein the one or more ultraviolet absorbing monomer that is incorporated in the polymer is art aromatic compound with olefinic functionality.

* * * * *